(12) United States Patent
Numazaki et al.

(10) Patent No.: US 8,101,179 B2
(45) Date of Patent: Jan. 24, 2012

(54) ANTI-CD20 MONOCLONAL ANTIBODY

(75) Inventors: Masanori Numazaki, Tokyo (JP); Tetsuo Nakamura, Tokyo (JP); Sadakazu Usuda, Tokyo (JP); Eduardo A. Padlan, Kensington, MD (US)

(73) Assignee: Biomedics Inc., Chuo-ku, Tokyo (JP)

( * ) Notice: Subject to any disclaimer, the term of this patent is extended or adjusted under 35 U.S.C. 154(b) by 816 days.

(21) Appl. No.: 11/910,429

(22) PCT Filed: Mar. 31, 2006

(86) PCT No.: PCT/JP2006/306925
§ 371 (c)(1),
(2), (4) Date: Oct. 1, 2007

(87) PCT Pub. No.: WO2006/106959
PCT Pub. Date: Oct. 12, 2006

(65) Prior Publication Data
US 2009/0197330 A1    Aug. 6, 2009

(30) Foreign Application Priority Data

Mar. 31, 2005  (JP) .................. 2005-103093
Dec. 28, 2005  (JP) .................. 2005-378466

(51) Int. Cl.
*A61K 39/395* (2006.01)
*C07K 16/28* (2006.01)
*C07K 16/30* (2006.01)
*C12N 5/20* (2006.01)
*C12N 5/10* (2006.01)

(52) U.S. Cl. ............... 424/133.1; 424/144.1; 424/153.1; 424/155.1; 424/156.1; 424/173.1; 424/174.1; 435/328; 435/343.1; 435/344; 435/344.1; 435/334; 435/358; 530/387.3; 530/388.22; 530/388.73; 530/388.8; 530/388.85

(58) Field of Classification Search .................. None
See application file for complete search history.

(56) References Cited

U.S. PATENT DOCUMENTS 6,565,827 B1 * 5/2003 Kaminski et al. ............ 424/1.49

FOREIGN PATENT DOCUMENTS

| JP | 10-179169 | 7/1998 |
|---|---|---|
| JP | 2001-074737 | 3/2001 |
| WO | WO 02/074251 | 9/2002 |
| WO | WO 03/068821 | 8/2003 |
| WO | WO 2005/000901 | 1/2005 |
| WO | WO 2005/044307 | 5/2005 |

OTHER PUBLICATIONS

Rudikoff et al. "Single amino acid substitution altering antigen binding specificity", Proceedings of the National Academy of Sciences, 1982. vol. 79, pp. 1979-1983.*

MacCallum et al. "Antibody-antigen interactions: contact analysis and binding site topography", Journal of Molecular Biology, 1996. vol. 262, pp. 732-745.*

De Pascalis et al. "Grafting of abbreviated complementarity determining regions containing specificity determining residues essential for ligand contact to engineer a less immunogenic humanized monoclonal antibody", Journal of Immunology, 2002. vol. 169, pp. 3076-3084.*

Anderson, et al. "Expression of Human B Cell-Associated Antigens on Leukemias and Lymphomas: A Model of Human B Cell Differentiation," *Blood*, vol. 63, No. 6, pp. 1424-1433, 1984.

Flieger, et al. "Mechanism of Cytotoxicity Induced by Chimeric Mouse Human Monoclonal Antibody IDEC-C2B8 in CD20-Expressing Lymphoma Cell Lines," *Cellular Immunology*, vol. 204, pp. 55-63, 2000.

Mathas, et al. "Anti-CD20- and B-cell Receptor-mediated Apoptosis: Evidence for Shared Intracellular Signaling Pathways," *Cancer Research*, vol. 60, pp. 7170-7176, 2000.

Cardarelli, et al. "Binding to CD20 by Anti-B1 Antibody or F(ab')$_2$ is Sufficient for Induction of Apoptosis in B-cell Lines," *Cancer Immunol. Immunother.*, vol. 51, pp. 15-24, 2002.

Pedersen, et al. "The Chimeric Anti-CD20 Antibody Rituximab Induces Apoptosis in B-Cell Chronic Lymphocytic Leukemia Cells Through a p38 Mitogen Activated Protein-Kinase-Dependent Mechanism," *Blood*, vol. 99, No. 4, pp. 1314-1319, 2002.

Deans, et al. "CD20-Mediated Apoptosis: Signalling Through Lipid Rafts," *Immunology*, vol. 107, pp. 176-182, 2002.

Golay, et al. "Independent Regulation of c-*myc*, B-*myb*, and c-*myb* Gene Expression by Inducers and Inhibitors of Proliferation in Human B Lymphocytes," *The Journal of Immunology*, vol. 149, No. 1, pp. 300-308, 1992.

Bourget, et al. "CD20 Monoclonal Antibodies Down-Regulate IgM at the Surface of B Cells," *Eur. J. Immunol.*, vol. 23, pp. 768-771, 1993.

White, et al. "Activation of Dense Human Tonsilar B Cells," *The Journal of Immunology*, vol. 146, No. 3, pp. 846-853, 1991.

Shan, et al. "Signaling Events Involved in Anti-CD20-Induced Apoptosis of Malignant Human B Cells," *Cancer Immunol. Immunother.*, vol. 48, pp. 673-683, 2000.

(Continued)

*Primary Examiner* — Ronald Schwadron
(74) *Attorney, Agent, or Firm* — Knobbe, Martens, Olson & Bear, LLP

(57) ABSTRACT

A murine anti-CD20 monoclonal antibody having cell growth inhibitory activities is disclosed. Cell growth inhibitory activities include apoptosis against human CD20 antigen expressing cells in culture of the CD20 antigen expressing cells without effector cells. The anti-CD20 monoclonal antibody is incorporated into chimeric anti-CD20 monoclonal antibodies in which the amino acid sequences of the variable regions of the anti-CD20 monoclonal antibody and the amino acid sequences of the constant regions of human immunoglobulin are fused. Also a humanized anti-CD20 monoclonal antibody is described which includes all of the variable region CDRs of the H chain of the anti-CD20 monoclonal antibody and all of the variable region CDRs of the L chain of the anti-CD20 monoclonal antibody and an amino acid sequence of human immunoglobulin. A nucleotide sequence encoding the amino acid sequence of the chimeric or humanized anti-CD20 monoclonal antibody can be expressed in mammalian cells.

10 Claims, 8 Drawing Sheets

OTHER PUBLICATIONS

Coiffier, et al. "Rituximab (Anti-CD20 Monoclonal Antibody) for the Treatment of Patients with Relapsing or Refractory Aggressive Lymphoma: A Multicenter Phase II Study," *Blood*, vol. 92, No. 6, pp. 1927-1932, 1998.

Edwards, et al. "Sustained Improvement in Rheumatoid Arthritis Following a Protocol Designed to Deplete B Lymphocytes," *Rheumatology*, vol. 40, pp. 205-211, 2001.

Zaja, et al. "B-Cell Depletion with Rituximab as Treatment for Immune Hemolytic Anemia and Chronic Thrombocytopenia," *Haematologica*, vol. 87, No. 2, pp. 189-195, 2002.

Perrotta, et al. "Anti-CD20 Monoclonal Antibody (Rituximab) for Life-Threatening Autoimmune Haemolytic Anaemia in a Patient with Systemic Lupus Erythematosus," *British Journal of Haematology*, vol. 116, pp. 465-467, 2002.

Polyak, et al. "Alanine-170 and Proline-172 are Critical Determinants for Extracellular CD20 Epitopes; Heterogeneity in the Fine Specificity of CD20 Monoclonal Antibodies is Defined by Additional Requirements Imposed by Both Amino Acid Sequence and Quaternary Structure," *Blood*, vol. 99, No. 9, pp. 3256-3262, 2002.

Miyamoto, et al. "Lymphocyte Proliferation Response During *Eimeria tenella* Infection Assessed by a New, Reliable, Nonradioactive Colorimetric Assay," *Avian Diseases*, vol. 46, pp. 10-16, 2002.

Ishida, et al. "The Expression Technology of Chimeric and Humanized Antibodies," *Nippon Rinsho*, vol. 60, No. 3, pp. 439-444, 2002.

Padlan, et al. "A Possible Procedure for Reducing the Immunogenicity of Antibody Variable Domains While Preserving Their Ligand-Binding Properties," *Molecular Immunology*, vol. 28, No. 4/5, pp. 489-498, 1991.

Wu, et al. "Possible Use of Similar Framework Region Amino Acid Sequences between Human and Mouse Immunoglobulins for Humanizing Mouse Antibodies," *Molecular Immunology*, vol. 29, No. 9, pp. 1141-1146, 1992.

Padlan, et al. "Identification of Specificity-Determining Residues in Antibodies," *FASEB J*, vol. 9, pp. 133-139, 1995.

Manches, et al. "In Vitro Mechanisms of Action of Rituximab on Primary Non-Hodgkin Lymphomas," *Blood*, vol. 101, No. 3, pp. 949-954, 2003.

Idusogie, et al. "Mapping of the C1q Binding Site on Rituxan, a Chimeric Antibody with a Human IgG1 Fc," *The Journal of Immunology*, vol. 164, pp. 4178-4184, 2000.

Aboagye-Mathiesen, et al. "Interferon Gamma Regulates a Unique Set of Proteins in Fresh Human Bladder Transitional Cell Carcinomas," *Electrophoresis*, vol. 20, pp. 344-348, 1999.

Oi, et al. "Immunoglobulin Producing Hybrid Cell Lines" in *Selected Methods in Cellular Immunology*, W.H. Freeman and Co., San Francisco, pp. 351-372, 1990.

Kim, et al. "Codon Optimization for High-Level Expression of Human Erythropoietin (EPO) in Mammalian Cells," *Gene*, vol. 199, pp. 293-301, 1997.

Shan, et al. "Synergistic Effects of the Fenretinide (4-HPR) and Anti-CD20 Monoclonal Antibodies on Apoptosis Induction of Malignant Human B Cells," *Clinical Cancer Research*, vol. 7, No. 8, pp. 2490-2495, Aug. 2001.

Davies, A.J., "Tositumomab and Iodine [$^{131}$I] Tositumomab in the Management of Follicular Lymphoma, An Oncologist's View," *Q.J. Nucl. Med. Mol. Imagining*, vol. 48, No. 4, pp. 305-316, 2004.

Stashenko, et al. "Characterization of a Human B Lymphocyte-Specific Antigen," *The Journal of Immunology*, vol. 125, No. 4, pp. 1678-1685, Oct. 1980.

Reff, et al. "Depletion of B Cells In Vivo by a Chimeric Mouse Human Monoclonal Antibody to CD20," *Blood*, vol. 83, No. 2, pp. 435-445, Jan. 15, 1994.

Uchida, et al. "The Innate Mononuclear Phagocyte Network Depletes B Lymphocytes Through Fc Receptor-Dependent Mechanisms During Anti-CD20 Antibody Immunotherapy," *J. Exp. Med.*, vol. 199, No. 12, pp. 1659-1669, Jun. 21, 2004.

Shan, et al. "Apoptosis of Malignant Human B Cells by Ligation of CD20 with Monoclonal Antibodies," *Blood*, vol. 91, No. 5, pp. 1644-1652, Mar. 1, 1998.

Smith, Mitchell R. "Rituximab (Monoclonal Anti-CD20 Antibody): Mechanisms of Action and Resistance," *Oncogene*, vol. 22, No. 47, pp. 7359-7368, Oct. 20, 2003.

Hofmeister, et al. "Clustered CD20 Induced Apoptosis: Src-Family Kinase, the Proximal Regulator of Tyrosine Phosphorylation, Calcium Influx, and Caspase 3-Dependent Apoptosis," *Blood Cells Mol. Dis*, vol. 26, No. 2, pp. 133-143, Apr. 2000.

Cragg, et al. "Complement-mediated Lysis by Anti-CD20 mAb Correlates with Segregation into Lipid Rafts," *Blood*, vol. 101, No. 3, pp. 1045-1052, Feb. 1, 2003.

Maloney, et al. "Phase I Clinical Trial Using Escalating Single-Dose Infusion of Chimeric Anti-CD20 Monoclonal Antibody (IDEC-C2B8) in Patients with Recurrent B-Cell Lymphoma," *Blood*, vol. 84, No. 8, pp. 2457-2466, Oct. 15, 1994.

Stein, et al. "Characterization of a New Humanized Anti-CD20 Monoclonal Antibody, IMMU-106, and its Use in Combination with the Humanized Anti-CD22 Antibody, Epratuzumab, for the Therapy of Non-Hodgkin's Lymphoma," *Clinical Cancer Research*, vol. 10, pp. 2868-2878, Apr. 15, 2004.

Teeling, et al. "Characterization of New Human CD20 Monoclonal Antibodies with Potent Cytolytic Activity Against non-Hodgkin Lymphomas," *Blood*, vol. 104, No. 6, pp. 1793-1800, Sep. 15, 2004.

Barclay, et al. *The Leukocyte Antigen Factsbook*, 2nd Edition, Academic Press, pp. 181-182, 1997.

\* cited by examiner

Human CD20 5' primer (SEQ ID NO: 13)
hCD20-S-GK-Not aatgcggccgccaccatgacaacacccagaaattc
Human CD20 3' primer (SEQ ID NO: 14)
hCD20-E-Xba gctctagattaaggagagctgtcattttc 1K1422 H chain V region sequence (SEQ ID NO: 1)
QVQLQQPGAELVKPGASVKMSCRASGYTFTNYNMHWIKQTPGQGLEWIGAIYPGSGDTSYNRKFKGKATLTADTS
SSTAYMQFSSLTSADSAVYYCARFTYYYGGTYGAMDYWGQGTSVTVSL 1K1791 H chain V region sequence (SEQ ID NO: 2)
QIQLVQSGPELKKPGETVKISCKASGYTFTNFGVNWVKQAPGKGLKWMGWINTYTGEPSYADDFKGRFAFSLEAS
ANTAYLQINNLKNDDMSTYFCTRRTNYYGTSYYYAMDYWGQGTSVTVSS 1K1712 H chain V region sequence (SEQ ID NO: 3)
QVQLQQPGAELVKPGASVKMSCKASGFTFTSYNLHWVKQTPGQGLEWIGAIYPGSGDTSYNQQFKGKATLTADKS
SNTAYMQLNSLTSEDSAVYCCARSAMISTGNWYFDYWGQGTTLTVSS 1K1402 H chain V region sequence (SEQ ID NO: 4)
QVQLQQPGAELVKPGASVKMSCKASGFTFTSYNMHWVKQTPGQGLEWIGGIYPGNGDTSYNQKFKGKATLTADKS
SSTAYMQLSSLTSEDSAVYYCARFYYYGSMGAMDYWGQGTSVTVSS 1K1736 H chain V region sequence (SEQ ID NO: 5)
QVQLQQPGAELVKPGASVKMSCKASGYTFTTYNLHWVKQTPGQGLEWIGGIYPGNGDTSYNQKFKVKATLTADKS
SNTAYMQLSSLTSEDSAVYYCARWIYYGNYEGTLDYWGQGTSVTVSS 1K1782 H chain V region sequence (SEQ ID NO: 6)
QVQLQQSGAELAKPGASVKMSCKASGYTFTSYWMHWVKQRPGQGLEWIGYITPSTGYTDYNKKFKDKATLTADRS
SSTAYMHLSSLTSEDSAVYYCARSGPYFDVWGAGTTVTVSS 1K1422 L chain V region sequence (SEQ ID NO: 7)
QIVLTQSPPIMSASLGEEITLTCSASSRVSYMLWYQQKSGTSPKLLIYSTSNLASGVPSRFSGSGSGTFYSLTIS
SVEAEDAADYYCHQWTSNPCTFGGGTKLEIK 1K1791 L chain V region sequence (SEQ ID NO: 8)
STVMTQTPKFLLVSAGDRVTITCKASQSVSNDVAWYQQKPGQSPKVLIYFASNRYTGVPDRFTGSGYGTDFTFTI
NTVQAEDLAVYFCQQDYSSPLTFGAGTKLELK 1K1712 L chain V region sequence (SEQ ID NO: 9)
QIVLSQSPAILSASPGEKVTMTCRASSSVSYMDWYQQKPGSSPKPWIYATSNLASGVPARFSGSGSGTSYSLTIS
RVEAEDTATYYCQQWTFNPPTFGSGTKLEIK 1K1402 L chain V region sequence (SEQ ID NO: 10)
QIVLSQSPAILSASPGEKVTMTCRASSSVSYMHWYQQKPGSSPKPWIYATSNLASGVPARFSGSGSGTSYSLTIT
RVEAEDAATYYCQQWTFNPPTFGAGTKLELK 1K1736 L chain V region sequence (SEQ ID NO: 11)
QIVLSQSPAILSSSPGEKVTMTCRASSSVSYMLWYQQKPGSSPEPWIYATSNLASGVPARFSGGGSGTSYSLTIS
RVEAEDAATYYCQQWTFNPPTFGGGTKLEIK 1K1782 L chain V region sequence (SEQ ID NO: 12)
DILLTQSPAILFVSPGERVSLSCRASQNIGTSIHWYQQRTNGSPRLLIKYASESFSGIPSRFSGSGSGTDFTLSI
NSVESEDIADYYCQQSNSWPFTFGSGTKLEIK 1K0924 H chain V region sequence (SEQ ID NO: 15)
QVQLQQPGAELVKPGASVKMSCKASGYTFTSYNIHWVKQTPGQGLEWIGAIYPGNGDTSYNQKFKGKATLTSDKS
SSTAYMQLSSLTSEDSAVYYCARMSTMITGFDYWGQGTTLTVSS 1K1228 H chain V region sequence (SEQ ID NO: 16)
QVQLQQPGAELVKPGASVKVSCKASGFTFTSYNLHWVKQTPGQGLVWIGAIYPGNGDTSYNQKFRGKATLTADIS
SSTAYMQLSSLTSEDSAVYYCARYYYGYDAMDYWGQGTSVTVSS 1K0924 L chain V region sequence (SEQ ID NO: 17)
QIVLSQSPAILSASPGEKVTMTCRASSSVSYMHWYQQRPGSSPKPWIYATSNLASGVPARFSGSGSGTSYYFTIS
RVEAEDAATYYCQQWNSNPPTHGGGTKLEIK 1K1228 L chain V region sequence (SEQ ID NO: 18)
EIILTQSPTTMAASPGEKITITCSASSSISSYYLRWYQQKPGFSPKVLIYRTSNLASGVPARFSGSGSGTSYSLTIG
TMEAEDVATYYCQQGNTVPLTFGSGTKLEIK

Fig. 4

Humanized antibody H chain V region sequence (abbH1791)(SEQ ID NO: 19)
QIQLVQSGSE LKKPGASVKV SCKASGYTFT NFGVNWVRQA PGKGLEWMGW INTYTGEPSY
AQGFTGRFVF SLDASVSTAY LQISSLKAED TATYFCTRRT NYYGTSYYYA MDYWGQGTTV
TVSS Humanized antibody H chain V region sequence example (abbH1791)(SEQ ID NO: 27)
ACTAGTTGCAGCTCCTATTTGGGTTCTTTCTCAGATCCAGCTGGTGCAGAGCGGCAGCGAGCTGAAGAAGCC
CGGCGCCAGCGTGAAGGTGAGCTGCAAGGCCAGCGGCTACACCTTCACCAACTTCGGCGTGAACTGGGTGCG
CCAGGCCCCCGGCAAGGGCCTGGAGTGGATGGGCTGGATCAACACCTACACCGGCGAGCCCAGCTACGCCCA
GGGCTTCACCGGCCGCTTCGTGTTCAGCCTGGACGCCAGCGTGAGCACCGCCTACCTGCAGATCAGCAGCCT
GAAGGCCGAGGACACCGCCACCTACTTCTGCACCCGCCGCACCAACTACTACGGCACCAGCTACTACTACGC
CATGGACTACTGGGGCCAGGGCACCACCGTGACCGTCTCGAGC Humanized antibody H chain V region sequence (fraH1791)(SEQ ID NO: 20)
QIQLVQSGSE LKKPGASVKV SCKASGYTFT NFGVNWVKQA PGKGLKWMGW INTYTGEPSY
ADDFKGRFAF SLDASASTAY LQISSLKAED MATYFCTRRT NYYGTSYYYA MDYWGQGTTV
TVSS Humanized antibody H chain V region sequence example (fraH1791)(SEQ ID NO: 28)
ACTAGTTGCAGCTCCTATTTGGGTTCTTTCTCAGATCCAGCTGGTGCAGAGCGGCAGCGAGCTGAAGAAGCC
CGGCGCCAGCGTGAAGGTGAGCTGCAAGGCCAGCGGCTACACCTTCACCAACTTCGGCGTGAACTGGGTGAA
GCAGGCCCCCGGCAAGGGCCTGAAGTGGATGGGCTGGATCAACACCTACACCGGCGAGCCCAGCTACGCCGA
CGACTTCAAGGGCCGCTTCGCCTTCAGCCTGGACGCCAGCGCCAGCACCGCCTACCTGCAGATCAGCAGCCT
GAAGGCCGAGGACATGGCCACCTACTTCTGCACCCGCCGCACCAACTACTACGGCACCAGCTACTACTACGC
CATGGACTACTGGGGCCAGGGCACCACCGTGACCGTCTCGAGC Humanized antibody H chain V region sequence (sdrH1791) (SEQ ID NO: 21)
QIQLVQSGSE LKKPGASVKV SCKASGYTFT NFGVNWVRQA PGKGLKWMGW INTYTGEPSY
AQGFTGRFAF SLDASVSTAY LQISSLKAED TATYFCTRRT NYYGTSYYYA MDYWGQGTTV
TVSS Humanized antibody H chain V region sequence example (sdrH1791)(SEQ ID NO: 29)
ACTAGTTGCAGCTCCTATTTGGGTTCTTTCTCAGATCCAGCTGGTGCAGAGCGGCAGCGAGCTGAAGAAGCC
CGGCGCCAGCGTGAAGGTGAGCTGCAAGGCCAGCGGCTACACCTTCACCAACTTCGGCGTGAACTGGGTGCG
CCAGGCCCCCGGCAAGGGCCTGAAGTGGATGGGCTGGATCAACACCTACACCGGCGAGCCCAGCTACGCCCA
GGGCTTCACCGGCCGCTTCGCCTTCAGCCTGGACGCCAGCGTGAGCACCGCCTACCTGCAGATCAGCAGCCT
GAAGGCCGAGGACACCGCCACCTACTTCTGCACCCGCCGCACCAACTACTACGGCACCAGCTACTACTACGC
CATGGACTACTGGGGCCAGGGCACCACCGTGACCGTCTCGAGC Humanized antibody H chain V region sequence (venH1791) (SEQ ID NO: 22)
QIQLVQSGPE LKKPGASVKI SCKASGYTFT NFGVNWVKQA PGKGLKWMGW INTYTGEPSY
ADDFKGRFAF SLDASVSTAY LQISSLKAED TSTYFCTRRT NYYGTSYYYA MDYWGQGTTV
TVSS Humanized antibody H chain V region sequence example (venH1791)(SEQ ID NO: 30)
ACTAGTTGCAGCTCCTATTTGGGTTCTTTCTCAGATCCAGCTGGTGCAGAGCGGCCCCGAGCTGAAGAAGCC
CGGCGCCAGCGTGAAGATCAGCTGCAAGGCCAGCGGCTACACCTTCACCAACTTCGGCGTGAACTGGGTGAA
GCAGGCCCCCGGCAAGGGCCTGAAGTGGATGGGCTGGATCAACACCTACACCGGCGAGCCCAGCTACGCCGA
CGACTTCAAGGGCCGCTTCGCCTTCAGCCTGGACGCCAGCGTGAGCACCGCCTACCTGCAGATCAGCAGCCT
GAAGGCCGAGGACACCAGCACCTACTTCTGCACCCGCCGCACCAACTACTACGGCACCAGCTACTACTACGC
CATGGACTACTGGGGCCAGGGCACCACCGTGACCGTCTCGAGC

Fig. 8A

Humanized antibody L chain V region sequence (abbL1791) (SEQ ID NO:23)
STVMTQSPDS LAVSLGERAT INCKSSQSVS NDVAWYQQKP GQSPKVLIYF ASNRYSGVPD
RFSGSGYGTD FTLTISSLQA EDVAVYFCQQ DYSSPLTFGA GTKLEIK
Humanized antibody L chain V region sequence example (abbL1791)(SEQ ID NO:31)
CCGCGGTGCCAGAAGCACCGTGATGACCCAGAGCCCCGACAGCCTGGCCGTGAGCCTGGGCGAGCGCGCCAC
CATCAACTGCAAGAGCAGCCAGAGCGTGAGCAACGACGTGGCCTGGTACCAGCAGAAGCCCGGCCAGAGCCC
CAAGGTGCTGATCTACTTCGCCAGCAACCGCTACAGCGGCGTGCCCGACCGCTTCAGCGGCAGCGGCTACGG
CACCGACTTCACCCTGACCATCAGCAGCCTGCAGGCCGAGGACGTGGCCGTGTACTTCTGCCAGCAGGACTA
CAGCAGCCCCCTGACCTTCGGCGCCGGCACCAAGCTGGAGATCAAGCGTACG Humanized antibody L chain V region sequence (fraL1791) (SEQ ID NO:24)
STVMTQSPSF LSASVGDRVT ITCKASQSVS NDVAWYQQKP GQSPKVLIYF ASNRYTGVPD
RFSGSGYGTD FTLTISSLQA EDVAVYFCQQ DYSSPLTFGA GTKLEIK
Humanized antibody L chain V region sequence example (fraL1791)(SEQ ID NO:32)
CCGCGGTGCCAGAAGCACCGTGATGACCCAGAGCCCCAGCTTCCTGAGCGCCAGCGTGGGCGACCGCGTGAC
CATCACCTGCAAGGCCAGCCAGAGCGTGAGCAACGACGTGGCCTGGTACCAGCAGAAGCCCGGCCAGAGCCC
CAAGGTGCTGATCTACTTCGCCAGCAACCGCTACACCGGCGTGCCCGACCGCTTCAGCGGCAGCGGCTACGG
CACCGACTTCACCCTGACCATCAGCAGCCTGCAGGCCGAGGACGTGGCCGTGTACTTCTGCCAGCAGGACTA
CAGCAGCCCCCTGACCTTCGGCGCCGGCACCAAGCTGGAGATCAAGCGTACG Humanized antibody L chain V region sequence (sdrL1791) (SEQ ID NO:25)
STVMTQSPDS LAVSLGERAT INCKSSQSNS NDVAWYQQKP GQSPKVLIYF ASNRYSGVPD
RFSGSGYGTD FTLTISSLQA EDVAVYFCQQ DYSSPLTFGA GTKLELK
Humanized antibody L chain V region sequence example (sdrL1791)(SEQ ID NO:33)
CCGCGGTGCCAGAAGCACCGTGATGACCCAGAGCCCCGACAGCCTGGCCGTGAGCCTGGGCGAGCGCGCCAC
CATCAACTGCAAGAGCAGCCAGAGCAACAGCAACGACGTGGCCTGGTACCAGCAGAAGCCCGGCCAGAGCCC
CAAGGTGCTGATCTACTTCGCCAGCAACCGCTACAGCGGCGTGCCCGACCGCTTCAGCGGCAGCGGCTACGG
CACCGACTTCACCCTGACCATCAGCAGCCTGCAGGCCGAGGACGTGGCCGTGTACTTCTGCCAGCAGGACTA
CAGCAGCCCCCTGACCTTCGGCGCCGGCACCAAGCTGGAGCTGAAGCGTACG Humanized antibody L chain V region sequence (venL1791) (SEQ ID NO:26)
STVMTQSPDS LAVSLGERVT INCKASQSVS NDVAWYQQKP GQSPKVLIYF ASNRYTGVPD
RFSGSGYGTD FTFTISSVQA EDVAVYFCQQ DYSSPLTFGA GTKLELK
Humanized antibody L chain V region sequence example (venL1791)(SEQ ID NO:34)
CCGCGGTGCCAGAAGCACCGTGATGACCCAGAGCCCCGACAGCCTGGCCGTGAGCCTGGGCGAGCGCGTGAC
CATCAACTGCAAGGCCAGCCAGAGCGTGAGCAACGACGTGGCCTGGTACCAGCAGAAGCCCGGCCAGAGCCC
CAAGGTGCTGATCTACTTCGCCAGCAACCGCTACACCGGCGTGCCCGACCGCTTCAGCGGCAGCGGCTACGG
CACCGACTTCACCTTCACCATCAGCAGCGTGCAGGCCGAGGACGTGGCCGTGTACTTCTGCCAGCAGGACTA
CAGCAGCCCCCTGACCTTCGGCGCCGGCACCAAGCTGGAGCTGAAGCGTACG

Fig. 8B

SEQUENCE LISTING

<160> NUMBER OF SEQ ID NOS: 34

<210> SEQ ID NO 1
<211> LENGTH: 123
<212> TYPE: PRT
<213> ORGANISM: Mus musculus

<400> SEQUENCE: 1

Gln Val Gln Leu Gln Gln Pro Gly Ala Glu Leu Val Lys Pro Gly Ala
1               5                   10                  15

Ser Val Lys Met Ser Cys Arg Ala Ser Gly Tyr Thr Phe Thr Asn Tyr
            20                  25                  30

Asn Met His Trp Ile Lys Gln Thr Pro Gly Gln Gly Leu Glu Trp Ile
        35                  40                  45

Gly Ala Ile Tyr Pro Gly Ser Gly Asp Thr Ser Tyr Asn Arg Lys Phe
    50                  55                  60

Lys Gly Lys Ala Thr Leu Thr Ala Asp Thr Ser Ser Thr Ala Tyr
65                  70                  75                  80

Met Gln Phe Ser Ser Leu Thr Ser Ala Asp Ser Ala Val Tyr Tyr Cys
                85                  90                  95

Ala Arg Phe Thr Tyr Tyr Tyr Gly Gly Thr Tyr Gly Ala Met Asp Tyr
            100                 105                 110

Trp Gly Gln Gly Thr Ser Val Thr Val Ser Leu
        115                 120

<210> SEQ ID NO 2
<211> LENGTH: 124
<212> TYPE: PRT
<213> ORGANISM: Mus musculus

<400> SEQUENCE: 2

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Val Asn Trp Val Lys Gln Ala Pro Gly Lys Gly Leu Lys Trp Met
        35                  40                  45

Gly Trp Ile Asn Thr Tyr Thr Gly Glu Pro Ser Tyr Ala Asp Asp Phe
    50                  55                  60

Lys Gly Arg Phe Ala Phe Ser Leu Glu Ala Ser Ala Asn Thr Ala Tyr
65                  70                  75                  80

Leu Gln Ile Asn Asn Leu Lys Asn Asp Asp Met Ser Thr Tyr Phe Cys
                85                  90                  95

Thr Arg Arg Thr Asn Tyr Tyr Gly Thr Ser Tyr Tyr Tyr Ala Met Asp
            100                 105                 110

Tyr Trp Gly Gln Gly Thr Ser Val Thr Val Ser Ser
        115                 120

<210> SEQ ID NO 3
<211> LENGTH: 122
<212> TYPE: PRT
<213> ORGANISM: Mus musculus

<400> SEQUENCE: 3

Gln Val Gln Leu Gln Gln Pro Gly Ala Glu Leu Val Lys Pro Gly Ala
1               5                   10                  15

Ser Val Lys Met Ser Cys Lys Ala Ser Gly Phe Thr Phe Thr Ser Tyr

```
                    20                  25                  30

Asn Leu His Trp Val Lys Gln Thr Pro Gly Gln Gly Leu Glu Trp Ile
            35                  40                  45

Gly Ala Ile Tyr Pro Gly Ser Gly Asp Thr Ser Tyr Asn Gln Gln Phe
        50                  55                  60

Lys Gly Lys Ala Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Cys Cys
                85                  90                  95

Ala Arg Ser Ala Met Ile Ser Thr Gly Asn Trp Tyr Phe Asp Tyr Trp
            100                 105                 110

Gly Gln Gly Thr Thr Leu Thr Val Ser Ser
            115                 120

<210> SEQ ID NO 4
<211> LENGTH: 121
<212> TYPE: PRT
<213> ORGANISM: Mus musculus

<400> SEQUENCE: 4

Gln Val Gln Leu Gln Gln Pro Gly Ala Glu Leu Val Lys Pro Gly Ala
1               5                   10                  15

Ser Val Lys Met Ser Cys Lys Ala Ser Gly Phe Thr Phe Thr Ser Tyr
            20                  25                  30

Asn Met His Trp Val Lys Gln Thr Pro Gly Gln Gly Leu Glu Trp Ile
            35                  40                  45

Gly Gly Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Phe Tyr Tyr Tyr Gly Ser Met Gly Ala Met Asp Tyr Trp Gly
            100                 105                 110

Gln Gly Thr Ser Val Thr Val Ser Ser
            115                 120

<210> SEQ ID NO 5
<211> LENGTH: 122
<212> TYPE: PRT
<213> ORGANISM: Mus musculus

<400> SEQUENCE: 5

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Thr Tyr
            20                  25                  30

Asn Leu His Trp Val Lys Gln Thr Pro Gly Gln Gly Leu Glu Trp Ile
            35                  40                  45

Gly Gly Ile Tyr Pro Gly Asn Gly Asp Thr Ser Tyr Asn Gln Lys Phe
        50                  55                  60

Lys Val Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Ile Tyr Tyr Gly Asn Tyr Glu Gly Thr Leu Asp Tyr Trp
            100                 105                 110
```

Gly Gln Gly Thr Ser Val Thr Val Ser Ser
        115                 120

<210> SEQ ID NO 6
<211> LENGTH: 116
<212> TYPE: PRT
<213> ORGANISM: Mus musculus

<400> SEQUENCE: 6

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Thr Pro Ser Thr Gly Tyr Thr Asp Tyr Asn Lys Lys Phe
    50                  55                  60

Lys Asp Lys Ala Thr Leu Thr Ala Asp Arg Ser Ser Thr Ala Tyr
65                  70                  75                  80

Met His Leu Ser Ser Leu Thr Ser Glu Asp Ser Ala Val Tyr Tyr Cys
            85                  90                  95

Ala Arg Ser Gly Pro Tyr Phe Asp Val Trp Gly Ala Gly Thr Thr Val
            100                 105                 110

Thr Val Ser Ser
        115

<210> SEQ ID NO 7
<211> LENGTH: 106
<212> TYPE: PRT
<213> ORGANISM: Mus musculus

<400> SEQUENCE: 7

Gln Ile Val Leu Thr Gln Ser Pro Pro Ile Met Ser Ala Ser Leu Gly
1               5                   10                  15

Glu Glu Ile Thr Leu Thr Cys Ser Ala Ser Ser Arg Val Ser Tyr Met
            20                  25                  30

Leu Trp Tyr Gln Gln Lys Ser Gly Thr Ser Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Thr Ser Asn Pro Cys Thr
            85                  90                  95

Phe Gly Gly Gly Thr Lys Leu Glu Ile Lys
            100                 105

<210> SEQ ID NO 8
<211> LENGTH: 107
<212> TYPE: PRT
<213> ORGANISM: Mus musculus

<400> SEQUENCE: 8

Ser Thr Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Val Leu Ile

```
                35                  40                  45
Tyr Phe Ala Ser Asn Arg Tyr Thr Gly Val Pro Asp Arg Phe Thr Gly
         50                  55                  60
Ser Gly Tyr Gly Thr Asp Phe Thr Phe Thr Ile Asn Thr Val Gln Ala
 65                  70                  75                  80
Glu Asp Leu Ala Val Tyr Phe Cys Gln Gln Asp Tyr Ser Ser Pro Leu
                 85                  90                  95
Thr Phe Gly Ala Gly Thr Lys Leu Glu Leu Lys
            100                 105
```

<210> SEQ ID NO 9
<211> LENGTH: 106
<212> TYPE: PRT
<213> ORGANISM: Mus musculus

<400> SEQUENCE: 9

```
Gln Ile Val Leu Ser Gln Ser Pro Ala Ile Leu Ser Ala Ser Pro Gly
  1               5                  10                  15
Glu Lys Val Thr Met Thr Cys Arg Ala Ser Ser Ser Val Ser Tyr Met
                 20                  25                  30
Asp Trp Tyr Gln Gln Lys Pro Gly Ser Ser Pro Lys Pro Trp Ile Tyr
             35                  40                  45
Ala Thr Ser Asn Leu Ala Ser Gly Val Pro Ala Arg Phe Ser Gly Ser
         50                  55                  60
Gly Ser Gly Thr Ser Tyr Ser Leu Thr Ile Ser Arg Val Glu Ala Glu
 65                  70                  75                  80
Asp Thr Ala Thr Tyr Tyr Cys Gln Gln Trp Thr Phe Asn Pro Pro Thr
                 85                  90                  95
Phe Gly Ser Gly Thr Lys Leu Glu Ile Lys
            100                 105
```

<210> SEQ ID NO 10
<211> LENGTH: 106
<212> TYPE: PRT
<213> ORGANISM: Mus musculus

<400> SEQUENCE: 10

```
Gln Ile Val Leu Ser Gln Ser Pro Ala Ile Leu Ser Ala Ser Pro Gly
  1               5                  10                  15
Glu Lys Val Thr Met Thr Cys Arg Ala Ser Ser Ser Val Ser Tyr Met
                 20                  25                  30
His Trp Tyr Gln Gln Lys Pro Gly Ser Ser Pro Lys Pro Trp Ile Tyr
             35                  40                  45
Ala Thr Ser Asn Leu Ala Ser Gly Val Pro Ala Arg Phe Ser Gly Ser
         50                  55                  60
Gly Ser Gly Thr Ser Tyr Ser Leu Thr Ile Thr Arg Val Glu Ala Glu
 65                  70                  75                  80
Asp Ala Ala Thr Tyr Tyr Cys Gln Gln Trp Thr Phe Asn Pro Pro Thr
                 85                  90                  95
Phe Gly Ala Gly Thr Lys Leu Glu Leu Lys
            100                 105
```

<210> SEQ ID NO 11
<211> LENGTH: 106
<212> TYPE: PRT
<213> ORGANISM: Mus musculus

<400> SEQUENCE: 11

```
Gln Ile Val Leu Ser Gln Ser Pro Ala Ile Leu Ser Ser Pro Gly
1               5                   10                  15

Glu Lys Val Thr Met Thr Cys Arg Ala Ser Ser Ser Val Ser Tyr Met
            20                  25                  30

Leu Trp Tyr Gln Gln Lys Pro Gly Ser Ser Pro Glu Pro Trp Ile Tyr
            35                  40                  45

Ala Thr Ser Asn Leu Ala Ser Gly Val Pro Ala Arg Phe Ser Gly Gly
        50                  55                  60

Gly Ser Gly Thr Ser Tyr Ser Leu Thr Ile Ser Arg Val Glu Ala Glu
65              70                  75                  80

Asp Ala Ala Thr Tyr Tyr Cys Gln Gln Trp Thr Phe Asn Pro Pro Thr
                85                  90                  95

Phe Gly Gly Gly Thr Lys Leu Glu Ile Lys
            100                 105

<210> SEQ ID NO 12
<211> LENGTH: 107
<212> TYPE: PRT
<213> ORGANISM: Mus musculus

<400> SEQUENCE: 12

Asp Ile Leu Leu Thr Gln Ser Pro Ala Ile Leu Phe Val Ser Pro Gly
1               5                   10                  15

Glu Arg Val Ser Leu Ser Cys Arg Ala Ser Gln Asn Ile Gly Thr Ser
            20                  25                  30

Ile His Trp Tyr Gln Gln Arg Thr Asn Gly Ser Pro Arg Leu Leu Ile
            35                  40                  45

Lys Tyr Ala Ser Glu Ser Phe Ser Gly Ile Pro Ser Arg Phe Ser Gly
        50                  55                  60

Ser Gly Ser Gly Thr Asp Phe Thr Leu Ser Ile Asn Ser Val Glu Ser
65              70                  75                  80

Glu Asp Ile Ala Asp Tyr Tyr Cys Gln Gln Ser Asn Ser Trp Pro Phe
                85                  90                  95

Thr Phe Gly Ser Gly Thr Lys Leu Glu Ile Lys
            100                 105

<210> SEQ ID NO 13
<211> LENGTH: 35
<212> TYPE: DNA
<213> ORGANISM: Artificial sequence
<220> FEATURE:
<223> OTHER INFORMATION: primer

<400> SEQUENCE: 13
aatgcggccg ccaccatgac aacacccaga aattc                            35

<210> SEQ ID NO 14
<211> LENGTH: 29
<212> TYPE: DNA
<213> ORGANISM: Artificial sequence
<220> FEATURE:
<223> OTHER INFORMATION: primer

<400> SEQUENCE: 14
gctctagatt aaggagagct gtcattttc                                   29

<210> SEQ ID NO 15
<211> LENGTH: 119
<212> TYPE: PRT
<213> ORGANISM: Mus musculus
```

<400> SEQUENCE: 15

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Ile His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
50                  55                  60

Lys Gly Lys Ala Thr Leu Thr Ser Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Met Ser Thr Met Ile Thr Gly Phe Asp Tyr Trp Gly Gln Gly
            100                 105                 110

Thr Thr Leu Thr Val Ser Ser
        115
```

<210> SEQ ID NO 16
<211> LENGTH: 119
<212> TYPE: PRT
<213> ORGANISM: Mus musculus

<400> SEQUENCE: 16

```
Gln Val Gln Leu Gln Gln Pro Gly Ala Glu Leu Val Lys Pro Gly Ala
1               5                   10                  15

Ser Val Lys Val Ser Cys Lys Ala Ser Gly Phe Thr Phe Thr Ser Tyr
            20                  25                  30

Asn Leu His Trp Val Lys Gln Thr Pro Gly Gln Gly Leu Val Trp Ile
        35                  40                  45

Gly Ala Ile Tyr Pro Gly Asn Gly Asp Thr Ser Tyr Asn Gln Lys Phe
50                  55                  60

Arg Gly Lys Ala Thr Leu Thr Ala Asp Ile Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Tyr Gly Tyr Asp Ala Met Asp Tyr Trp Gly Gln Gly
            100                 105                 110

Thr Ser Val Thr Val Ser Ser
        115
```

<210> SEQ ID NO 17
<211> LENGTH: 106
<212> TYPE: PRT
<213> ORGANISM: Mus musculus

<400> SEQUENCE: 17

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Arg Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Tyr Phe Thr Ile Ser Arg Val Glu Ala Glu
65                  70                  75                  80
```

Asp Ala Ala Thr Tyr Tyr Cys Gln Gln Trp Asn Ser Asn Pro Pro Thr
                85                  90                  95

His Gly Gly Gly Thr Lys Leu Glu Ile Lys
            100                 105

<210> SEQ ID NO 18
<211> LENGTH: 108
<212> TYPE: PRT
<213> ORGANISM: Mus musculus

<400> SEQUENCE: 18

Glu Ile Ile Leu Thr Gln Ser Pro Thr Thr Met Ala Ala Ser Pro Gly
1               5                   10                  15

Glu Lys Ile Thr Ile Thr Cys Ser Ala Ser Ser Ile Ser Ser Tyr
            20                  25                  30

Tyr Leu Arg Trp Tyr Gln Gln Lys Pro Gly Phe Ser Pro Lys Val Leu
            35                  40                  45

Ile Tyr Arg Thr Ser Asn Leu Ala Ser Gly Val Pro Ala Arg Phe Ser
        50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Asn Thr Val Pro
                85                  90                  95

Leu Thr Phe Gly Ser Gly Thr Lys Leu Glu Ile Lys
            100                 105

<210> SEQ ID NO 19
<211> LENGTH: 124
<212> TYPE: PRT
<213> ORGANISM: Artificial Sequence
<220> FEATURE:
<223> OTHER INFORMATION: Humanized variable region designed based on
      mouse variable region

<400> SEQUENCE: 19

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Gly Val Asn Trp Val Arg Gln Ala Pro Gly Lys Gly Leu Glu Trp Met
            35                  40                  45

Gly Trp Ile Asn Thr Tyr Thr Gly Glu Pro Ser Tyr Ala Gln Gly Phe
        50                  55                  60

Thr Gly Arg Phe Val Phe Ser Leu Asp Ala Ser Val Ser Thr Ala Tyr
65                  70                  75                  80

Leu Gln Ile Ser Ser Leu Lys Ala Glu Asp Thr Ala Thr Tyr Phe Cys
                85                  90                  95

Thr Arg Arg Thr Asn Tyr Tyr Gly Thr Ser Tyr Tyr Ala Met Asp
            100                 105                 110

Tyr Trp Gly Gln Gly Thr Thr Val Thr Val Ser Ser
        115                 120

<210> SEQ ID NO 20
<211> LENGTH: 124
<212> TYPE: PRT
<213> ORGANISM: Artificial Sequence
<220> FEATURE:
<223> OTHER INFORMATION: Humanized variable region designed based on
      mouse variable region -continued

```
<400> SEQUENCE: 20

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Gly Val Asn Trp Val Lys Gln Ala Pro Gly Lys Gly Leu Lys Trp Met
        35                  40                  45

Gly Trp Ile Asn Thr Tyr Thr Gly Glu Pro Ser Tyr Ala Asp Asp Phe
    50                  55                  60

Lys Gly Arg Phe Ala Phe Ser Leu Asp Ala Ser Ala Ser Thr Ala Tyr
65                  70                  75                  80

Leu Gln Ile Ser Ser Leu Lys Ala Glu Asp Met Ala Thr Tyr Phe Cys
                85                  90                  95

Thr Arg Arg Thr Asn Tyr Tyr Gly Thr Ser Tyr Tyr Tyr Ala Met Asp
            100                 105                 110

Tyr Trp Gly Gln Gly Thr Thr Val Thr Val Ser Ser
        115                 120

<210> SEQ ID NO 21
<211> LENGTH: 124
<212> TYPE: PRT
<213> ORGANISM: Artificial Sequence
<220> FEATURE:
<223> OTHER INFORMATION: Humanized variable region designed based on
      mouse variable region

<400> SEQUENCE: 21

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Gly Val Asn Trp Val Arg Gln Ala Pro Gly Lys Gly Leu Lys Trp Met
        35                  40                  45

Gly Trp Ile Asn Thr Tyr Thr Gly Glu Pro Ser Tyr Ala Gln Gly Phe
    50                  55                  60

Thr Gly Arg Phe Ala Phe Ser Leu Asp Ala Ser Val Ser Thr Ala Tyr
65                  70                  75                  80

Leu Gln Ile Ser Ser Leu Lys Ala Glu Asp Thr Ala Thr Tyr Phe Cys
                85                  90                  95

Thr Arg Arg Thr Asn Tyr Tyr Gly Thr Ser Tyr Tyr Tyr Ala Met Asp
            100                 105                 110

Tyr Trp Gly Gln Gly Thr Thr Val Thr Val Ser Ser
        115                 120

<210> SEQ ID NO 22
<211> LENGTH: 124
<212> TYPE: PRT
<213> ORGANISM: Artificial Sequence
<220> FEATURE:
<223> OTHER INFORMATION: Humanized variable region designed based on
      mouse variable region

<400> SEQUENCE: 22

Gln Ile Gln Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr Asn Phe
            20                  25                  30

Gly Val Asn Trp Val Lys Gln Ala Pro Gly Lys Gly Leu Lys Trp Met
        35                  40                  45
```

```
Gly Trp Ile Asn Thr Tyr Thr Gly Glu Pro Ser Tyr Ala Asp Asp Phe
    50                  55                  60

Lys Gly Arg Phe Ala Phe Ser Leu Asp Ala Ser Val Ser Thr Ala Tyr
65                  70                  75                  80

Leu Gln Ile Ser Ser Leu Lys Ala Glu Asp Thr Ser Thr Tyr Phe Cys
                85                  90                  95

Thr Arg Arg Thr Asn Tyr Tyr Gly Thr Ser Tyr Tyr Ala Met Asp
                100                 105                 110

Tyr Trp Gly Gln Gly Thr Thr Val Thr Val Ser Ser
        115                 120
```

<210> SEQ ID NO 23
<211> LENGTH: 159
<212> TYPE: PRT
<213> ORGANISM: Artificial Sequence
<220> FEATURE:
<223> OTHER INFORMATION: Humanized variable region designed based on
      mouse variable region

<400> SEQUENCE: 23

```
Ser Thr Val Met Thr Gln Ser Pro Asp Ser Leu Ala Val Ser Leu Gly
1               5                   10                  15

Glu Arg Ala Thr Ile Asn Cys Lys Ser Ser Gln Ser Val Ser Asn Asp
                20                  25                  30

Val Ala Trp Tyr Gln Gln Lys Pro Gly Gln Ser Pro Lys Val Leu Ile
            35                  40                  45

Tyr Phe Ala Ser Asn Arg Tyr Ser Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Phe Cys Gln Gln Asp Tyr Ser Ser Pro Leu
                85                  90                  95

Thr Phe Gly Ala Gly Thr Lys Leu Glu Ile Lys Cys Ala Gly Cys Ala
                100                 105                 110

Gly Cys Cys Cys Cys Cys Thr Gly Ala Cys Cys Thr Thr Cys Gly Gly
            115                 120                 125

Cys Gly Cys Cys Gly Gly Cys Ala Cys Cys Ala Ala Gly Cys Thr Gly
        130                 135                 140

Gly Ala Gly Ala Thr Cys Ala Ala Gly Cys Gly Thr Ala Cys Gly
145                 150                 155
```

<210> SEQ ID NO 24
<211> LENGTH: 107
<212> TYPE: PRT
<213> ORGANISM: Artificial Sequence
<220> FEATURE:
<223> OTHER INFORMATION: Humanized variable region designed based on
      mouse variable region

<400> SEQUENCE: 24

```
Ser Thr Val Met Thr Gln Ser Pro Ser Phe Leu Ser Ala Ser Val Gly
1               5                   10                  15

Asp Arg Val Thr Ile Thr Cys Lys Ala Ser Gln Ser Val Ser Asn Asp
                20                  25                  30

Val Ala Trp Tyr Gln Gln Lys Pro Gly Gln Ser Pro Lys Val Leu Ile
            35                  40                  45

Tyr Phe Ala Ser Asn Arg Tyr Thr Gly Val Pro Asp Arg Phe Ser Gly
    50                  55                  60
```

```
Ser Gly Tyr Gly Thr Asp Phe Thr Leu Thr Ile Ser Ser Leu Gln Ala
 65                  70                  75                  80

Glu Asp Val Ala Val Tyr Phe Cys Gln Gln Asp Tyr Ser Ser Pro Leu
                 85                  90                  95

Thr Phe Gly Ala Gly Thr Lys Leu Glu Ile Lys
            100                 105

<210> SEQ ID NO 25
<211> LENGTH: 107
<212> TYPE: PRT
<213> ORGANISM: Artificial Sequence
<220> FEATURE:
<223> OTHER INFORMATION: Humanized variable region designed based on
      mouse variable region

<400> SEQUENCE: 25

Ser Thr Val Met Thr Gln Ser Pro Asp Ser Leu Ala Val Ser Leu Gly
 1               5                  10                  15

Glu Arg Ala Thr Ile Asn Cys Lys Ser Ser Gln Ser Asn Ser Asn Asp
                20                  25                  30

Val Ala Trp Tyr Gln Gln Lys Pro Gly Gln Ser Pro Lys Val Leu Ile
            35                  40                  45

Tyr Phe Ala Ser Asn Arg Tyr Ser Gly Val Pro Asp Arg Phe Ser Gly
 50                  55                  60

Ser Gly Tyr Gly Thr Asp Phe Thr Leu Thr Ile Ser Ser Leu Gln Ala
 65                  70                  75                  80

Glu Asp Val Ala Val Tyr Phe Cys Gln Gln Asp Tyr Ser Ser Pro Leu
                 85                  90                  95

Thr Phe Gly Ala Gly Thr Lys Leu Glu Leu Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: Humanized variable region designed based on
      mouse variable region

<400> SEQUENCE: 26

Ser Thr Val Met Thr Gln Ser Pro Asp Ser Leu Ala Val Ser Leu Gly
 1               5                  10                  15

Glu Arg Val Thr Ile Asn Cys Lys Ala Ser Gln Ser Val Ser Asn Asp
                20                  25                  30

Val Ala Trp Tyr Gln Gln Lys Pro Gly Gln Ser Pro Lys Val Leu Ile
            35                  40                  45

Tyr Phe Ala Ser Asn Arg Tyr Thr Gly Val Pro Asp Arg Phe Ser Gly
 50                  55                  60

Ser Gly Tyr Gly Thr Asp Phe Thr Phe Thr Ile Ser Ser Val Gln Ala
 65                  70                  75                  80

Glu Asp Val Ala Val Tyr Phe Cys Gln Gln Asp Tyr Ser Ser Pro Leu
                 85                  90                  95

Thr Phe Gly Ala Gly Thr Lys Leu Glu Leu Lys
            100                 105

<210> SEQ ID NO 27
<211> LENGTH: 403
<212> TYPE: DNA
<213> ORGANISM: Artificial Sequence
<220> FEATURE:
<223> OTHER INFORMATION: Humanized variable region designed based on
``` mouse variable region

<400> SEQUENCE: 27

```
actagttgca gctcctattt gggttctttc tcagatccag ctggtgcaga gcggcagcga      60
gctgaagaag cccggcgcca gcgtgaaggt gagctgcaag gccagcggct acaccttcac     120
caacttcggc gtgaactggg tgcgccaggc cccggcaag ggcctggagt ggatgggctg      180
gatcaacacc tacaccggcg agcccagcta cgcccagggc ttcaccggcc gcttcgtgtt     240
cagcctggac gccagcgtga gcaccgccta cctgcagatc agcagcctga aggccgagga     300
caccgccacc tacttctgca cccgccgcac caactactac ggcaccagct actactacgc     360
catggactac tggggccagg gcaccaccgt gaccgtctcg agc                        403
```

<210> SEQ ID NO 28
<211> LENGTH: 403
<212> TYPE: DNA
<213> ORGANISM: Artificial Sequence
<220> FEATURE:
<223> OTHER INFORMATION: Humanized variable region designed based on
      mouse variable region

<400> SEQUENCE: 28

```
actagttgca gctcctattt gggttctttc tcagatccag ctggtgcaga gcggcagcga      60
gctgaagaag cccggcgcca gcgtgaaggt gagctgcaag gccagcggct acaccttcac     120
caacttcggc gtgaactggg tgaagcaggc cccggcaag ggcctgaagt ggatgggctg      180
gatcaacacc tacaccggcg agcccagcta cgccgacgac ttcaagggcc gcttcgcctt     240
cagcctggac gccagcgcca gcaccgccta cctgcagatc agcagcctga aggccgagga     300
catggccacc tacttctgca cccgccgcac caactactac ggcaccagct actactacgc     360
catggactac tggggccagg gcaccaccgt gaccgtctcg agc                        403
```

<210> SEQ ID NO 29
<211> LENGTH: 403
<212> TYPE: DNA
<213> ORGANISM: Artificial Sequence
<220> FEATURE:
<223> OTHER INFORMATION: Humanized variable region designed based on
      mouse variable region

<400> SEQUENCE: 29

```
actagttgca gctcctattt gggttctttc tcagatccag ctggtgcaga gcggcagcga      60
gctgaagaag cccggcgcca gcgtgaaggt gagctgcaag gccagcggct acaccttcac     120
caacttcggc gtgaactggg tgcgccaggc cccggcaag ggcctgaagt ggatgggctg      180
gatcaacacc tacaccggcg agcccagcta cgcccagggc ttcaccggcc gcttcgcctt     240
cagcctggac gccagcgtga gcaccgccta cctgcagatc agcagcctga aggccgagga     300
caccgccacc tacttctgca cccgccgcac caactactac ggcaccagct actactacgc     360
catggactac tggggccagg gcaccaccgt gaccgtctcg agc                        403
```

<210> SEQ ID NO 30
<211> LENGTH: 403
<212> TYPE: DNA
<213> ORGANISM: Artificial Sequence
<220> FEATURE:
<223> OTHER INFORMATION: Humanized variable region designed based on
      mouse variable region

<400> SEQUENCE: 30

```
actagttgca gctcctattt gggttctttc tcagatccag ctggtgcaga gcggccccga      60
```

```
gctgaagaag cccggcgcca gcgtgaagat cagctgcaag gccagcggct acaccttcac    120
caacttcggc gtgaactggg tgaagcaggc ccccggcaag ggcctgaagt ggatgggctg    180
gatcaacacc tacaccggcg agcccagcta cgccgacgac ttcaagggcc gcttcgcctt    240
cagcctggac gccagcgtga gcaccgccta cctgcagatc agcagcctga aggccgagga    300
caccagcacc tacttctgca cccgccgcac caactactac ggcaccagct actactacgc    360
catggactac tggggccagg gcaccaccgt gaccgtctcg agc                      403
```

<210> SEQ ID NO 31
<211> LENGTH: 340
<212> TYPE: DNA
<213> ORGANISM: Artificial Sequence
<220> FEATURE:
<223> OTHER INFORMATION: Humanized variable region designed based on
      mouse variable region

<400> SEQUENCE: 31

```
ccgcggtgcc agaagcaccg tgatgaccca gcccccgac agcctggccg tgagcctggg    60
cgagcgcgcc accatcaact gcaagagcag ccagagcgtg agcaacgacg tggcctggta   120
ccagcagaag cccggccaga gccccaaggt gctgatctac ttcgccagca accgctacag   180
cggcgtgccc gaccgcttca gcggcagcgg ctacggcacc gacttcaccc tgaccatcag   240
cagcctgcag gccgaggacg tggccgtgta cttctgccag caggactaca gcagccccct   300
gaccttcggc gccggcacca agctggagat caagcgtacg                         340
```

<210> SEQ ID NO 32
<211> LENGTH: 340
<212> TYPE: DNA
<213> ORGANISM: Artificial Sequence
<220> FEATURE:
<223> OTHER INFORMATION: Humanized variable region designed based on
      mouse variable region

<400> SEQUENCE: 32

```
ccgcggtgcc agaagcaccg tgatgaccca gcccccagc ttcctgagcg ccagcgtggg    60
cgaccgcgtg accatcacct gcaaggccag ccagagcgtg agcaacgacg tggcctggta   120
ccagcagaag cccggccaga gccccaaggt gctgatctac ttcgccagca accgctacac   180
cggcgtgccc gaccgcttca gcggcagcgg ctacggcacc gacttcaccc tgaccatcag   240
cagcctgcag gccgaggacg tggccgtgta cttctgccag caggactaca gcagccccct   300
gaccttcggc gccggcacca agctggagat caagcgtacg                         340
```

<210> SEQ ID NO 33
<211> LENGTH: 340
<212> TYPE: DNA
<213> ORGANISM: Artificial Sequence
<220> FEATURE:
<223> OTHER INFORMATION: Humanized variable region designed based on
      mouse variable region

<400> SEQUENCE: 33

```
ccgcggtgcc agaagcaccg tgatgaccca gcccccgac agcctggccg tgagcctggg    60
cgagcgcgcc accatcaact gcaagagcag ccagagcaac agcaacgacg tggcctggta   120
ccagcagaag cccggccaga gccccaaggt gctgatctac ttcgccagca accgctacag   180
cggcgtgccc gaccgcttca gcggcagcgg ctacggcacc gacttcaccc tgaccatcag   240
cagcctgcag gccgaggacg tggccgtgta cttctgccag caggactaca gcagccccct   300
```

```
gaccttcggc gccggcacca agctggagct gaagcgtacg              340

<210> SEQ ID NO 34
<211> LENGTH: 340
<212> TYPE: DNA
<213> ORGANISM: Artificial Sequence
<220> FEATURE:
<223> OTHER INFORMATION: Humanized variable region designed based on
      mouse variable region

<400> SEQUENCE: 34
ccgcggtgcc agaagcaccg tgatgaccca gagccccgac agcctggccg tgagcctggg    60
cgagcgcgtg accatcaact gcaaggccag ccagagcgtg agcaacgacg tggcctggta   120
ccagcagaag cccggccaga gcccaaggt gctgatctac ttcgccagca accgctacac   180
cggcgtgccc gaccgcttca gcggcagcgg ctacggcacc gacttcacct tcaccatcag   240
cagcgtgcag gccgaggacg tggccgtgta cttctgccag caggactaca gcagccccct   300
gaccttcggc gccggcacca agctggagct gaagcgtacg              340
```

ANTI-CD20 MONOCLONAL ANTIBODY

RELATED APPLICATIONS

This application is the U.S. National Phase under 35 U.S.C. §371 of International Application PCT/JP2006/306925, filed Mar. 31, 2006, which was published in a non-English language, which claims priority to JP Application No. 2005-103093, filed Mar. 31, 2005 and JP Application No. 2005-378466, filed Dec. 28, 2005.

TECHNICAL FIELD

The present invention relates to a monoclonal antibody directed to the human CD20 antigen. The present invention further relates to a chimeric anti-CD20 monoclonal antibody and a humanized anti-CD20 monoclonal antibody produced by gene recombination, as well as a therapeutic agent for a B cell-mediated tumor or an immunological disease containing either of these antibodies as an active ingredient.

BACKGROUND ART

As monoclonal antibodies that recognize the CD20 antigen, B1, 2B8 (chimeric antibody name is rituximab), 1F5, 2H7 and so forth are known. Above all, rituximab, a chimeric anti-CD20 monoclonal antibody developed by IDEC Pharmaceuticals Corporation, U.S., has been established as a standard therapeutic agent for low malignancy non-Hodgkin's lymphoma (NHL), and found to have a therapeutic effect on many B cell-mediated immunological diseases. For example, it is said to be effective for, in addition to malignant tumors such as chronic lymphatic leukemia, autoimmune diseases in which a pathogenic autoantibody appears to be involved such as autoimmune hemolytic anemia and idiopathic thrombocytopenia purpura, and inflammatory diseases such as chronic rheumatoid arthritis and multiple sclerosis (Non-patent documents 14 to 17).

CD20 is a molecule present on the B lymph cell surface and expression thereof is seen in normal B cells in peripheral blood, spleen, tonsil and bone marrow and so forth as well as B cells in most of malignant tumors. This molecule comprises 297 amino acid residues, penetrates a cell membrane four times, and has both the C-terminus and N-terminus inside the cell, and has the only extracellularly exposed loop with no sugar chain consisting of 43 amino acid residues between the third and fourth transmembrane domains (Non-patent documents 1 and 9). The CD20 molecule is thought to usually exist as a tetramer, and further form a heterocomplex with other minor components (Non-patent document 18). Since the CD20 protein is not secreted out of the cell or cleaved, and in addition, it is hardly taken up into the cell by antibody binding, it can be expected that a cytotoxic mechanism based on an antibody directed to it against a target cell effectively works (Non-patent documents 1 to 3).

In spite of the small molecular size thereof, CD20 shows diversity of epitope partly due to the effect of the expression form thereof as a complex outside the cell, and antibodies binding to it mediate variously different biological responses. For example, activities such as down-regulation of B cell receptors, increase of expressions of MHC class II antigens and adhesion molecules, activation of $Ca^{2+}$ release in the presence of hyper-cross-linking, inhibition of lymphocyte function-associated antigen 1 non-dependent homotypic adhesion, induction of apoptosis and the opposite activity, promotion of cell growth, vary significantly (Non-patent documents 4 to 13). The typical examples of anti-CD20 antibody, rituximab, B1, 1F5 and 2H7, also have different characteristics and biological functions, and a reference to a "monoclonal antibody binding to CD20" alone cannot specify the biological properties thereof.

The molecule that constitutes the extracellular domain of CD20 is insoluble. Although the CD20 molecule derived from a cell lysate or as a gene recombinant protein can be solubilized by using a surfactant or strong alkali, it is difficult to maintain the natural three-dimensional structure under such a treatment condition. Therefore, a CD20 positive B cell strain is used as an immunogen for obtaining antibodies. However, immunostimulating property thereof is weak, and it is not easy to obtain clones of mature antibody-producing cells.

As of 2005, rituximab, a mouse/human chimeric antibody, is the only anti-CD20 monoclonal antibody approved as a therapeutic agent. Since chimeric molecules with heterologous molecules have antigenicity, they are not generally preferred as therapeutic agents. However, anti-CD20 antibodies have a property of targeting and eliminating all B cells including normal cells, and therefore they are said to have substantially no antigenicity. However, examples have been reported in which a neutralizing antibody is induced during the treatment period, although they account for only several percents, and it would become more likely to be induced depending on the dose and dosing period. Therefore, development of a humanized antibody having a sequence closer to that of human or a human antibody is desired. Another disadvantage of chimeric antibodies is the short blood half-life, and β half-life is only 3 or 4 days. The effective rate of rituximab alone against recurrence of low malignancy NHL was a little lower than 50% in a clinical study in the United States, indicating that 50% or more patients do not respond or poorly respond to rituximab. The response rate in patients with moderate malignancy NHL is even lower, being only about 30% (Non-patent document 14). Therefore, it is necessary to investigate the factors and background of the different responses in patients, and development of an antibody having a superior effect is desired at the same time.

Non-patent document 1: Leukocyte Fact Book 2nd Edition, Academic Press

Non-patent document 2: Stashenko P et al., J. Immunol., 1980, 125: 1678-85

Non-patent document 3: Anderson K C et al., Blood, 1984, 63:

Non-patent document 4: Shan D et al., Blood, 1998, 91: 1644

Non-patent document 5: Flieger D et al., Cell Immunol., 2000, 204: 55-63

Non-patent document 6: Mathas S et al., Cancer Res., 2000, 60: 7170-6

Non-patent document 7: Cardarelli P M et al., Cancer Immunol. Immunother., 2002, 51: 15-24

Non-patent document 8: Pedersen I M et al., Blood, 2002, 99:

Non-patent document 9: Deans J P et al., Immunol., 2002, 107:

Non-patent document 10: Golay J T et al., J. Immunol., 1992, 149: 300-8

Non-patent document 11: Bourger I et al., Eur. J. Immunol., 1993, 23: 768-71

Non-patent document 12: White M W et al., J. Immunol., 1991, 146: 846-53

Non-patent document 13: Shan D et al., Cancer Immunol. Immunother., 2000, 48: 673-83

Non-patent document 14: Coiffier B et al., Blood, 1998, 92:

Non-patent document 15: Edward J C et al., Rheumatology (Oxford), 2001, 40: 205-11

Non-patent document 16: Zaja F et al., Heamatologica, 2002, 87: 189-95

Non-patent document 17: Perrotta S et al., Br. J. Haematol., 2002, 116: 465-7

Non-patent document 18: Polyak M J et al., Blood, 2002, 99: 3256-62

DISCLOSURE OF THE INVENTION

An object of the present invention is to provide a monoclonal antibody having biological functions superior to those of conventional anti-CD20 monoclonal antibody therapeutic agents.

The inventors of the present invention obtained murine anti-CD20 monoclonal antibodies that specifically bind to the human CD20 antigen by using two or more CD20 antigen positive B cell strains, mammalian cells biotechnologically made to express the human CD20 antigen on cell membranes thereof, and the human CD20 protein fused with glutathione S-transferase (GST) protein in an arbitrary combination as an immunogen. Some of them had direct cell growth inhibitory activities including apoptosis in an in vitro CD20 expressing cell culture without effector cells. Further, irrespective of the presence or absence of the cell growth inhibitory activities such as apoptosis, these antibodies, including other selected murine anti-CD20 monoclonal antibodies, were imparted with effective complement- or antibody-dependent cell-mediated cytotoxicity by chimerization. By humanizing the amino acid sequences of the antibodies determined to have the most desirable biological activities among them, anti-CD20 monoclonal antibodies that could be used as a therapeutic agent were prepared. The present invention was thus accomplished.

The present invention provides the followings.
(1) A murine anti-CD20 monoclonal antibody having cell growth inhibitory activities including apoptosis against human CD20 antigen expressing cells in culture of the CD20 antigen expressing cells without effector cells.
(2) The anti-CD20 monoclonal antibody according to (1), wherein the amino acid sequences of the H chain variable region and the L chain variable region are SEQ ID NOS: 1 and 7, SEQ ID NOS: 2 and 8, or SEQ ID NOS: 15 and 17.
(3) A hybridoma producing the anti-CD20 monoclonal antibody according to (1) or (2).
(4) A chimeric anti-CD20 monoclonal antibody, wherein the amino acid sequence of the variable region of the anti-CD20 monoclonal antibody according to (2) and the amino acid sequence of the constant region of human immunoglobulin are fused.
(5) An anti-CD20 monoclonal antibody humanized by using the amino acid sequence of the complementarity determining region (CDR) of the variable region of the anti-CD20 monoclonal antibody according to (2) and an amino acid sequence of human immunoglobulin.
(6) The humanized anti-CD20 monoclonal antibody according to (5), wherein the combination of the amino acid sequences of the H chain variable region and the L chain variable region is a combination of SEQ ID NOS: 19 and 23, SEQ ID NOS: 19 and 24, SEQ ID NOS: 19 and 25, SEQ ID NOS: 19 and 26, SEQ ID NOS: 20 and 23, SEQ ID NOS: 20 and 24, SEQ ID NOS: 20 and 25, SEQ ID NOS: 20 and 26, SEQ ID NOS: 21 and 23, SEQ ID NOS: 21 and 24, SEQ ID NOS: 21 and 25, SEQ ID NOS: 21 and 26, SEQ ID NOS: 22 and 23, SEQ ID NOS: 22 and 24, SEQ ID NOS: 22 and 25, or SEQ ID NOS: 22 and 26.
(7) The anti-CD20 monoclonal antibody according to any one of (4) to (6), which has cytotoxicity against CD20 antigen expressing cells in the presence of a human complement.
(8) A mammalian cell incorporated with a nucleotide sequence encoding the amino acid sequence of the anti-CD20 monoclonal antibody according to any one of (4) to (7).
(9) The mammalian cell according to (8), which is a Chinese hamster ovary (CHO) cell.
(10) A murine anti-CD20 monoclonal antibody, wherein the combination of the amino acid sequences of the H chain variable region and the L chain variable region is a combination of SEQ ID NOS: 3 and 9, SEQ ID NOS: 4 and 10, SEQ ID NOS: 5 and 11, SEQ ID NOS: 6 and 12, or SEQ ID NOS: 16 and 18.
(11) A hybridoma producing the anti-CD20 monoclonal antibody according to (10).
(12) A chimeric anti-CD20 monoclonal antibody, wherein the amino acid sequence of the variable region of the anti-CD20 monoclonal antibody according to (10) and the amino acid sequence of the constant region of human immunoglobulin are fused.
(13) An anti-CD20 monoclonal antibody humanized by using the amino acid sequence of the variable region CDR of the anti-CD20 monoclonal antibody according to (10) and an amino acid sequence of human immunoglobulin.
(14) The anti-CD20 monoclonal antibody according to (12) or (13), which has cytotoxicity against CD20 antigen expressing cells in the presence of a human complement.
(15) A mammalian cell incorporated with a nucleotide sequence encoding the amino acid sequence of the anti-CD20 monoclonal antibody according to any one of (12) to (14).
(16) The mammalian cell according to (15), which is a CHO cell.
(17) A diagnostic agent comprising the anti-CD20 monoclonal antibody according to any one of (2), (4) to (7), (10) and (12) to (14) as an active ingredient.
(18) A therapeutic agent comprising the anti-CD20 monoclonal antibody according to any one of (4) to (7) and (12) to (14) as an active ingredient.

Amino acid residues in the amino acid sequences of the monoclonal antibodies defined above may be replaced with other amino acid residues so long as the secondary structures and biological properties thereof are not significantly altered, and such monoclonal antibodies of which amino acid sequences are changed as mentioned above also fall in the scope of the present invention.

BRIEF DESCRIPTION OF THE DRAWINGS

FIG. 4 Amino acid sequences of H chain and L chain variable regions of murine anti-CD20 monoclonal antibodies.

FIGS. 5A and B show culture days 1 and 2, respectively, at antibody concentration of 2 μg/ml. FIGS. 5C and D show culture days 1 and 2, respectively, at antibody concentration of 4 μg/ml.

FIG. 8A Amino acid sequences of H chain and L chain variable regions of humanized anti-CD20 monoclonal antibodies and nucleotide sequences corresponding to them.

FIG. 8B Amino acid sequences of H chain and L chain variable regions of humanized anti-CD20 monoclonal antibodies and nucleotide sequences corresponding to them.

BEST MODE FOR CARRYING OUT THE INVENTION

Figure 1:
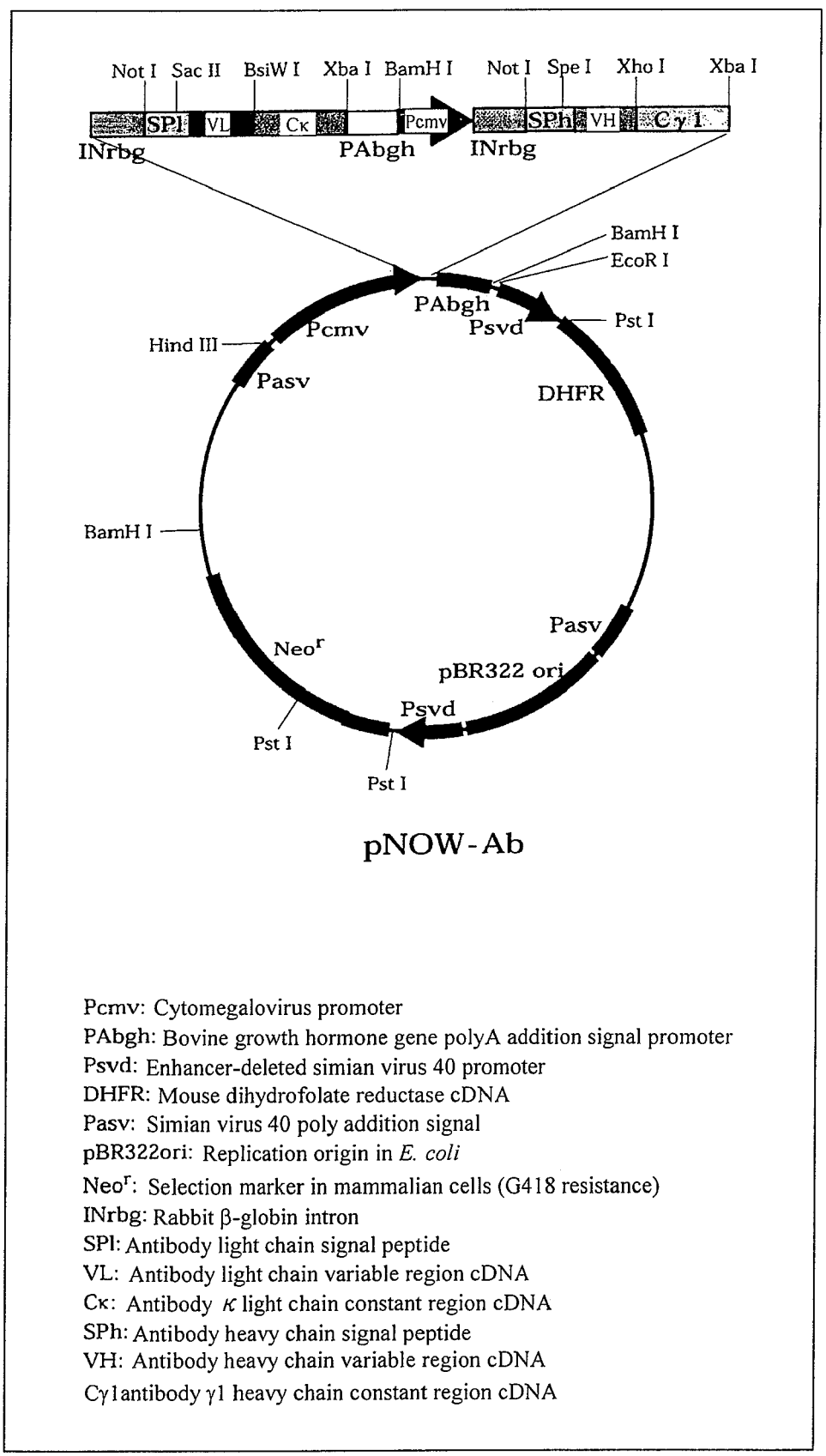
FIG. 1 Structure of a vector for expressing a recombinant antibody, pNOW-Ab.

In the present invention, the term "antibody" is used in a meaning that encompasses antibody in the general meaning, H chain and L chain constituting it, and fragments thereof.

The present invention relates to an anti-CD20 monoclonal antibody that binds to the human CD20 antigen on a cell membrane and has biological activities desirable for inducing a therapeutic effect.

The antibody according to a first embodiment of the present invention is a monoclonal antibody that specifically binds to the human CD20 antigen on a cell membrane and has cell growth inhibitory activities including apoptosis against human CD20 antigen expressing cells in culture of the CD20 antigen expressing cells without the aid of effector cells. This is originally a murine anti-CD20 monoclonal antibody, and further includes an anti-CD20 monoclonal antibody obtained by chimerizing or humanizing that antibody. These antibodies have direct cell growth inhibitory activities including apoptosis against human CD20 antigen expressing cells in in vitro culture of the CD20 antigen expressing cells without the aid of effector cells. These chimerized or humanized anti-CD20 monoclonal antibodies have a complement- and/or antibody-dependent cell-mediated cytotoxicity.

The binding property to a CD20 antigen on a cell membrane can be examined by cell-ELISA, in which CD20 expressing cells such as SB cells and Raji cells are adhered to a plate and reacted with a monoclonal antibody to be tested. However, since expression levels of the CD20 antigen of these cells are insufficient, the reactivity is not high. Therefore, in the present invention, a method of cell-ELISA was developed, in which CHO cells in which CD20 is expressed in a large amount by gene recombination (CD20/CHO cells) are adhered to a plate and reacted with a monoclonal antibody to be tested. In a preliminary test of the present invention, it was confirmed that cell-ELISA using the CD20/CHO cells showed a pattern similar to that observed in cell-ELISA using the SB cells or Raji cells in a reactivity test of a monoclonal antibody, and showed high sensitivity (see the example, Establishment of CD20/CHO cell ELISA screening method, Table 1).

The direct cell growth inhibitory activities in an in vitro culture of human CD20 antigen expressing cells without effector cells can be determined by a usual method (Miyamoto T et al., Avian Dis., Vol. 46(1), 10-16). Further, the apoptosis inducing ability can be determined by a test using flow cytometry (annexin V/propidium iodide (PI) staining).

Examples of the antibody according to the first embodiment include mouse anti-CD20 monoclonal antibodies having a combination of the amino acid sequences of SEQ ID NOS: 1 and 7, SEQ ID NOS: 2 and 8, or SEQ ID NOS: 15 and 17 for the H chain variable region and the L chain variable region, as well as anti-CD20 monoclonal antibodies obtained by chimerizing or humanizing those antibodies. These antibodies exhibit direct cell growth inhibitory activities including apoptosis against human CD20 antigen expressing cells in in vitro culture of the CD20 antigen expressing cells without the aid of effector cells. These antibodies also have complement- and/or antibody-dependent cell-mediated cytotoxicity. The present invention also includes a hybridoma producing a murine antibody, and a mammalian cell (CHO cell in the examples) incorporated with a nucleotide sequence corresponding to any one of the amino acid sequences of the chimeric or humanized antibodies.

Chimerization is carried out by fusing the amino acid sequence of the H chain variable region of a murine monoclonal antibody and the amino acid sequence of the H chain constant region of human immunoglobulin, and the amino acid sequence of the L chain variable region and the amino acid sequence of the L chain constant region of human immunoglobulin (Ishida T et al., Nippon Rinsho, Vol. 60, No 3, 439-444). Humanized antibodies are designed by using an amino acid sequence of the variable region CDR of a murine monoclonal antibody and an amino acid sequence of human immunoglobulin. Humanized anti-CD20 monoclonal antibodies preferred as therapeutic agents are selected by comparing characteristics of variously designed antibodies (Padlan EA, Mol. Immunol., Vol. 28, No 4/5, 489-498; Wu T T and Kabat EA, Mol. Immunol., Vol. 29, No 9, 1141-1146; Padlan E A et al., FASEB J., Vol. 9, 133-139).

Chimerized or humanized anti-CD20 monoclonal antibodies further have complement-dependent cytotoxicity (CDC), and antibody-dependent cell-mediated cytotoxicity (ADCC) in the presence of effector cells. As for test methods for these CDC and ADCC, commonly used methods can be referred to (Manches O et al., Blood, 2003, 101(3), 949-54; Idusogie E E et al., J. Immunol., 2000, 164, 4178-4184).

Specific examples of the humanized anti-CD20 monoclonal antibodies include those having a combination of the amino acid sequences of SEQ ID NOS: 19 and 23, SEQ ID NOS: 19 and 24, SEQ ID NOS: 19 and 25, SEQ ID NOS: 19 and 26, SEQ ID NOS: 20 and 23, SEQ ID NOS: 20 and 24, SEQ ID NOS: 20 and 25, SEQ ID NOS: 20 and 26, SEQ ID NOS: 21 and 23, SEQ ID NOS: 21 and 24, SEQ ID NOS: 21 and 25, SEQ ID NOS: 21 and 26, SEQ ID NOS: 22 and 23, SEQ ID NOS: 22 and 24, SEQ ID NOS: 22 and 25, or SEQ ID NOS: 22 and 26 for the H chain variable region and the L chain variable region.

The antibody according to a second embodiment of the present invention is a murine monoclonal antibody that specifically binds to the human CD20 antigen on a cell membrane, and does not exhibit cell growth inhibitory activities including apoptosis or exhibit such activities at a level not so high. However, these murine antibodies can be imparted with CDC or ADCC activity by chimerization or humanization. These cytotoxic activities are also important biological activities, and therefore the anti-CD20 monoclonal antibody of the second embodiment can also be a promising candidate of therapeutic agent.

Examples of the antibody according to the second embodiment include murine anti-CD20 monoclonal antibodies having a combination of the amino acid sequences of SEQ ID NOS: 3 and 9, SEQ ID NOS: 4 and 10, SEQ ID NOS: 5 and 11, SEQ ID NOS: 6 and 12, or SEQ ID NOS: 16 and 18 for the H chain variable region and the L chain variable region, as well as anti-CD20 monoclonal antibodies obtained by chimerizing or humanizing those antibodies. The present invention also includes a hybridoma producing the murine antibody, and a mammalian cell (CHO cells in the example) incorporated with a nucleotide sequence corresponding to any one of the amino acid sequences of the chimeric or humanized antibodies.

The method for determining binding property to the CD20 antigen on a cell membrane, various test methods for determining cell growth inhibition, apoptosis, ADCC, CDC, and so forth, and the preparation method for chimeric or humanized antibodies are similar to those mentioned for the antibody of the first embodiment.

Both the chimeric anti-CD20 monoclonal antibody and humanized anti-CD20 monoclonal antibody described as the antibodies of the first embodiment and the second embodiment can be expected to exhibit superior effect as a therapeutic agent for B cell-mediated malignant tumors and immunological diseases in which B cells or antibodies produced by B cells are involved, and an object of the present invention is to use them in development of a therapeutic agent containing either a chimeric or humanized anti-CD20 monoclonal antibody, desirably a humanized anti-CD20 monoclonal antibody, as an active ingredient. Examples of the objective diseases include non-Hodgkin's lymphoma, Hodgkin's lymphoma, chronic lymphatic leukemia, acute lymphatic leukemia, chronic rheumatoid arthritis, autoimmune hemolytic anemia, idiopathic thrombocytopenia purpura, systemic lupus erythematosus, anti-phospholipid antibody syndrome, Sjogren's syndrome, Crohn's disease, scleroderma, multiple sclerosis, type I diabetes, and so forth.

The murine monoclonal antibody of the present invention can be prepared by the following method.

As an immunogen for sensitization, the SB cell or Raji cell as a cell strain that expresses the human CD20 antigen, and CHO cell made to express the human CD20 antigen can be used in combination. Further, a human CD20 protein fused with GST (GST-CD20) may be used as a complementary sensitizing antigen.

A hybridoma producing a monoclonal antibody can be prepared by a series of procedures including (1) immunization of an animal to be immunized (mouse), (2) preparation of lymphocytes from the immunized animal, (3) preparation of parent cells, (4) cell fusion of the lymphocytes and the parent cells, (5) screening and (6) cloning (Biochemistry Experiment Method: Monoclonal antibody, written by Ailsa M. Campbell, translated by Toshiaki Osawa, Tokyo Kagaku Dozin Co., Ltd., 1989). An anti-CD20 monoclonal antibody that specifically binds to the CD20 antigen on a cell surface can be cloned by reacting a monoclonal antibody to be tested with a cell-ELISA system in which CD20/CHO cells are immobilized on a plate. Commercially available expression vectors can also be used. However, since the CD20 antigen needs to be expressed on the CHO cell at a high density, a mammalian cell high expression vector, pNOW (Japanese Patent No. 3582965) may be used. A selection criterion of the monoclonal antibody is exhibition of reactivity comparable to or higher than that of a positive control.

A chimerized or humanized antibody can be prepared according to a usual gene recombination method. For example, pNOW-Ab, which contains 2 sets of multicloning sites positioned in tandem for producing the antibody, and is incorporated beforehand with the genes encoding human H chain and the L chain constant regions, can be used as an expression vector (FIG. 1).

EXAMPLE 1

Preparation, chimerization and humanization of monoclonal antibodies directed to the CD20 antigen as well as test for characteristics of the obtained antibodies will be explained below with reference to the examples.

(1) Preparation of Immunogen for Sensitizing Mouse

Figures 2, 3:
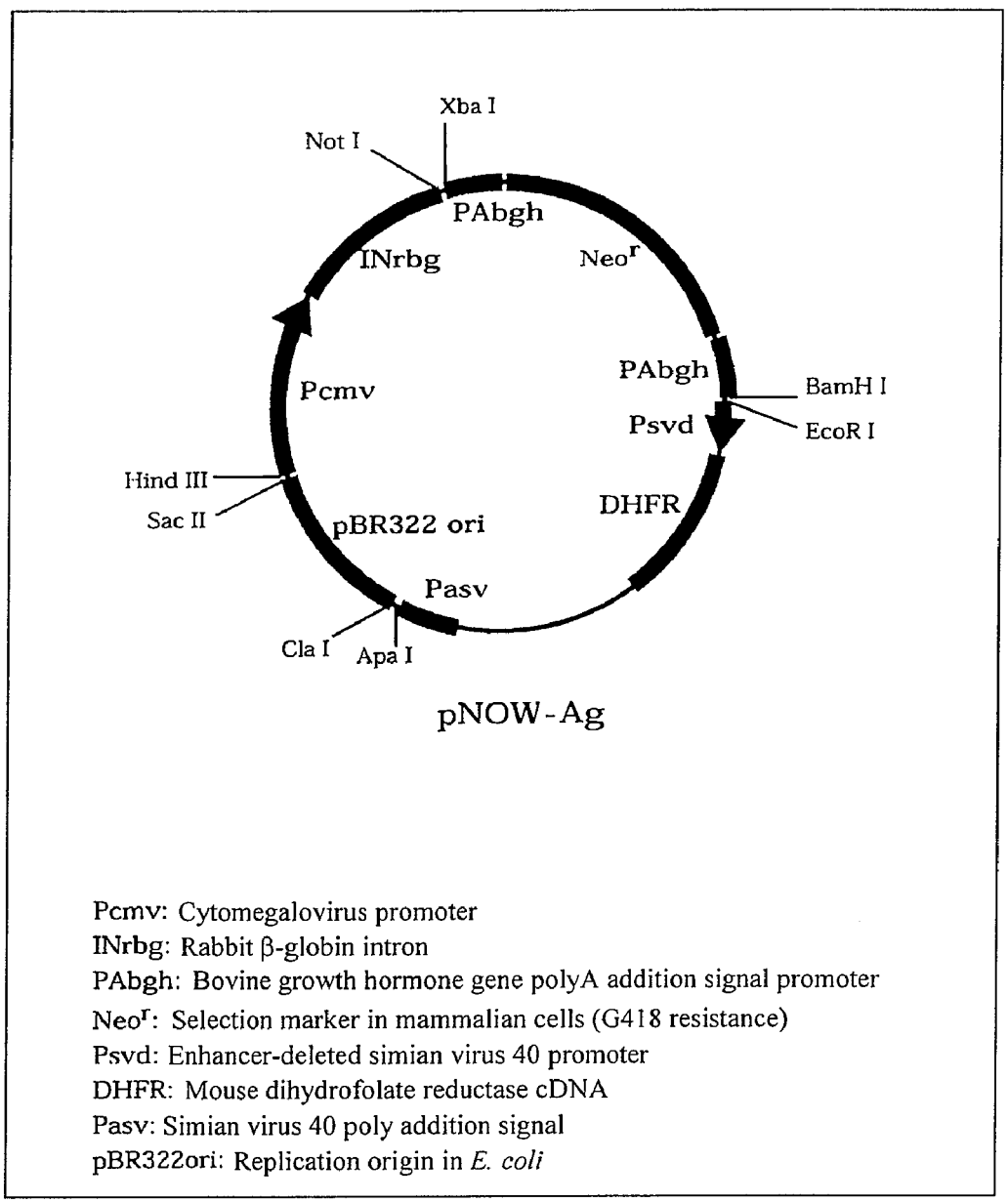
FIG. 2 Structure of a vector for expressing a protein, pNOW-Ag.
FIG. 3 Sequences of primers for cloning human CD20 gene.

The human CD20 gene was obtained from a cDNA library by using a 5' primer of SEQ ID NO: 13 and a 3' primer of SEQ ID NO: 14, which are specific to the gene encoding the total molecule of human CD20 (Multiple Choice cDNA human spleen, Origene Technologies, Inc., 6 Taft Court, Suite 100, Rockville, Md. 20850). Specifically, the primers shown in FIG. 3 were used. The CD20 gene was incorporated into pNOW-Ag (FIG. 2) as a high expression vector for mammalian cells, and transfected into CHO cells as the host cells. Recombinant CHO cells (CD20/CHO cells) expressing CD20 molecules at a high level on their cell surfaces were established by FACS analysis. Cells showing 5 or more times higher fluorescence intensity compared with the SB cell in staining with FITC-labeled anti-CD20 monoclonal antibodies were defined as those showing high expression. GST-CD20, the complementary immunogen, was prepared by fusing GST at the N terminus of 43 amino acid residues of the CD20 extracellular domain by using the pGEX-4T2 vector (G et al. AM, Electrophoresis, Vol. 20(2): 344-348).

(2) Preparation of Immunogen

The SB cells or Raji cells were cultured in 10% FCS-added RPMI 1640 medium. The CD20/CHO cells were cultured in CHO—S—SFM II medium (GIBCO, Cat. No. 12052-098) added with 800 μg/ml of G418. These cultures were centrifuged (1100 rpm, 5 minutes), then the cells were added with Dulbecco's PBS(−) and suspended, and the suspension was centrifuged again. This washing procedure was repeated once again, and a suspension prepared by adding physiological saline to the cells (cell count: 1 to $3 \times 10^7$/ml) was used for immunization. pGEX-4T2 incorporated with GST-CD20 was introduced into *E. coli* competent cells. The competent cells were lysed after culture, and GST-CD20 was crudely purified from the lysed cells, and then solubilized by addition of 0.1 N sodium hydroxide.

(3) Immunization and Cell Fusion

As animals to be immunized, 7- to 11-week old Balb/c female mice were used. The SB cells, Raji cells or CD20/CHO cells were repeatedly administered twice or three times at intervals of various numbers of days, then a different cell antigen (SB cells, Raji cells or CD20/CHO cells) was selected and used for the final immunization. The count of cells administered was 1 to $3 \times 10^7$ per mouse regardless of the cell type. Further, complementary immunization was performed by using GST-CD20 for a part of the mice. Three days after the final immunization, spleen cells were extracted from the mice, and suspended in the RPMI medium, and a fusion reaction with mouse myeloma (NS-1) was carried out in the presence of PEG-1500 (Qi, V T et. Herzenberg, 1980, in: Selected Methods in Cellular Immunology; Mishell B et al. (Freeman and Co., San Francisco, Calif.) p. 351).

(4) Establishment of CD20/CHO Cell-ELISA Screening Method

Several murine anti-CD20 monoclonal antibodies and 2B8 were reacted by using 96-well plates to which the SB cells, Raji cells, CD20/CHO cells and CD20 CHO parent cell line were adhered. It was confirmed that in these cell-ELISA tests, similar tendencies were observed for the antibody concentrations, and it was found that relative comparisons between the antibodies and with a control were also possible. Because of the high density of the surface cell antigens adhered to the plate in the CD20/CHO cell-ELISA, an absorbance was observed at a level sufficiently enabling the detection even with a relatively low concentration of the test antibody sample, and it was found to be a sensitive measurement system. The specific measurement results are shown in Table 1.

TABLE 1

Comparison of SB cell-ELISA, Raji cell-ELISA and CD20/CHO cell-ELISA

| Antibody | Raji cell-ELISA (A492) Antibody concentration (ng/ml) | | | | | | SB cell-ELISA (A492) Antibody concentration (ng/ml) | | | | | |
|---|---|---|---|---|---|---|---|---|---|---|---|---|
| | 1000 | 320 | 100 | 32 | 10 | 3 | 1000 | 320 | 100 | 32 | 10 | 3 |
| 1K1228 | 1.683 | 1.170 | 0.678 | 0.326 | 0.148 | nt | 1.265 | 0.931 | 0.452 | 0.192 | 0.082 | Nt |
| 1K1257 | 1.775 | 1.263 | 0.782 | 0.445 | 0.177 | 0.096 | 1.509 | 1.143 | 0.570 | 0.276 | 0.119 | 0.055 |
| 1K1402 | 1.228 | 0.525 | 0.214 | 0.102 | 0.061 | 0.049 | 0.763 | 0.400 | 0.152 | 0.095 | 0.066 | 0.057 |
| 1K1422 | 0.748 | 0.277 | 0.121 | 0.057 | 0.046 | 0.049 | 0.403 | 0.147 | 0.071 | 0.039 | 0.036 | 0.051 |
| 1K1428 | 1.196 | 0.514 | 0.222 | 0.104 | 0.067 | 0.057 | 1.111 | 0.509 | 0.252 | 0.108 | 0.058 | 0.061 |
| 1K1436A | 0.887 | 0.376 | 0.191 | 0.105 | 0.058 | 0.058 | 0.959 | 0.445 | 0.264 | 0.120 | 0.067 | 0.065 |
| 2B8 | 0.329 | 0.121 | 0.055 | 0.038 | 0.034 | 0.046 | 0.337 | 0.091 | 0.045 | 0.038 | 0.037 | 0.053 |
| NC | 0.035 | | | | | | 0.028 | | | | | |

| Antibody | CD20/CHO cell-ELISA (A492) Antibody concentration (ng/ml) | | | | | | CHO cell-ELISA (parent cell line) (A492) Antibody concentration (ng/ml) | | | | | |
|---|---|---|---|---|---|---|---|---|---|---|---|---|
| | 1000 | 320 | 100 | 32 | 10 | 3 | 1000 | 320 | 100 | 32 | 10 | 3 |
| 1K1228 | 3.056 | 2.704 | 2.091 | 1.275 | 0.572 | 0.265 | 0.081 | 0.040 | 0.038 | 0.034 | 0.038 | Nt |
| 1K1257 | 3.184 | 2.576 | 1.924 | 1.223 | 0.604 | 0.271 | 0.095 | 0.053 | 0.038 | 0.039 | 0.037 | 0.029 |
| 1K1402 | 1.877 | 1.574 | 1.486 | 0.824 | 0.389 | 0.174 | 0.385 | 0.170 | 0.085 | 0.063 | 0.070 | 0.065 |
| 1K1422 | 2.230 | 1.327 | 0.842 | 0.238 | 0.105 | 0.068 | 0.164 | 0.068 | 0.046 | 0.047 | 0.035 | 0.067 |
| 1K1428 | 2.544 | 2.448 | 2.190 | 0.967 | 0.463 | 0.283 | 0.564 | 0.213 | 0.091 | 0.056 | 0.050 | 0.060 |
| 1K1436A | 2.432 | 2.369 | 2.278 | 1.101 | 0.559 | 0.286 | 0.375 | 0.153 | 0.072 | 0.043 | 0.043 | 0.060 |
| 2B8 | 2.293 | 1.664 | 1.090 | 0.561 | 0.174 | 0.089 | 0.056 | 0.040 | 0.045 | 0.035 | 0.044 | 0.060 |
| NC | 0.070 | | | | | | 0.029 | | | | | |

(5) Screening by Cell-ELISA

Cell-ELISA was performed by using a 96-well plate to which the CD20/CHO cells or CHO cells (CD20 parent cell line) were adhered, and wells were selected in which antibodies specifically reactive to CD20 were produced. 2B8 was used as a positive control, and a mouse monoclonal antibody directed to the human CD3 antigen (BD PharMingen) was used as a negative control. Specifically, the CD20/CHO cells or CHO cells (parent cell line) adhered to a poly-L-lysine coated 96-well plate (Asahi Techno Glass Corporation, Cat. No. 11-023-018) were used for cell-ELISA. A blocking solution (0.2% gelatin and 0.5% BSA solution in PBS) was added in a volume of 150 μl to each well and left standing at 37° C. for 1 hour. Then, the plate was washed 5 times with 150 mM NaCl and 0.05% Tween 20 aqueous solution, and 100 μl of each sample (diluted solution of culture supernatant) was added to each well to perform the primary reaction at 37° C. for 1 hour. After washing, 100 μl of a diluted solution of a labeled antibody [HRP-labeled anti-mouse IgG(H+L) rabbit antibody (Jackson Lab., Code No. 315-035-003) or HRP-labeled anti-mouse IgG(Fcγ) rabbit antibody (Jackson Lab., Code No. 315-035-008)] was added to each well to perform the secondary reaction at 37° C. for 1 hour. For the preparation of the reaction mixtures for the primary and secondary reactions, a solution the same as the blocking solution was used. After washing, 100 μl of a color development solution (OPD) was added to each well, 30 minutes later, 50 μl of 4 N $H_2SO_4$ was added to terminate the reaction, and absorbance was measured at 492 nm (A492). Then, wells showing reactivity comparable to or significantly higher than that of 2B8 were selected.

(6) Cloning

Cloning was carried out by the limited dilution method. Cells were seeded on a 96-well plate and cultured, then cell-ELISA for CD20/CHO cells was performed for culture supernatant of a well containing 1 colony to select a clone producing a specific antibody.

(7) Preparation of Purified Antibody

The clone producing a specific antibody was cultured in 10% FCS-added RPMI 1640 medium. When the cell density became about $5 \times 10^5$/ml, the medium was replaced with a serum-free medium, ASF-104N (Ajinomoto Co. Inc.), and culture were continued. Then, 2 to 4 days later, the culture medium was centrifuged, and the culture supernatant was collected and subjected to purification using a protein G column. The eluted monoclonal antibody solution was dialyzed against 150 mM NaCl. The solution was subjected to filtration sterilization using a filter having a pore size of 0.2 um and used as a test antibody (anti-human CD20 mouse monoclonal antibody).

Monoclonal antibody clones showing binding affinity comparable to that of the positive control were selected by the CD20/CHO cell-ELISA. The gene sequences of variable regions of these antibodies were determined, and the amino acid sequences thereof were determined as a result. The sequences of the H chain variable region and the L chain variable region of typical antibodies are shown in SEQ ID NOS: 1 and 7, SEQ ID NOS: 2 and 8, SEQ ID NOS: 3 and 9, SEQ ID NOS: 4 and 10, SEQ ID NOS: 5 and 11, SEQ ID NOS: 6 and 12, SEQ ID NOS: 15 and 17, and SEQ ID NOS: 16 and 18 (FIG. 4). Further, biological characteristics of these clones were investigated.

Biological Characteristic Test (1): Apoptosis Induction Test

The apoptosis inducing ability of the test antibodies was determined by flow cytometry (annexin V/PI staining). 2B8 was used as a positive control, and the mouse monoclonal antibody directed to the human CD3 (BD PharMingen) was used as a negative control. The procedures were as follows.

MEBCYTO Apoptosis Kit (MBL, Cat. No. 4700, Lot. 20) was used.

The Raji cells were centrifuged, and then suspended in a fresh RPMI 1640 medium (Sigma, Cat. No. R8758, Lot 44K2416) containing 10% FCS (inactivated) (ICN, Cat. No. 2916754, Lot 8005C), and 1 ml of the suspension at a density of $5 \times 10^5$ cells/ml was added to each well of a 12-well plate. Twelve wells were used for each antibody, and each antibody was added at a final concentration of 2 μg/ml or 4 μg/ml (3 wells×2 different concentrations×2 time points, 12 wells in total).

One day and two days after the start of the culture, the culture medium containing about $2\times10^5$ cells was collected, and centrifuged, and then the cells were washed once with PBS. Subsequently, 85 μl of a binding buffer was added to the cells to suspend the cells in the buffer. Further, to the suspension was added 10 μl of annexin V-FITC and 5 μl of PI, mixed sufficiently, and allowed to react at room temperature for 15 minutes with light shielding.

Measurement was performed by flow cytometry (FACS Calibur, Becton Dickinson), and the results were analyzed by using CellQuest (Becton Dickinson).

Figure 5:
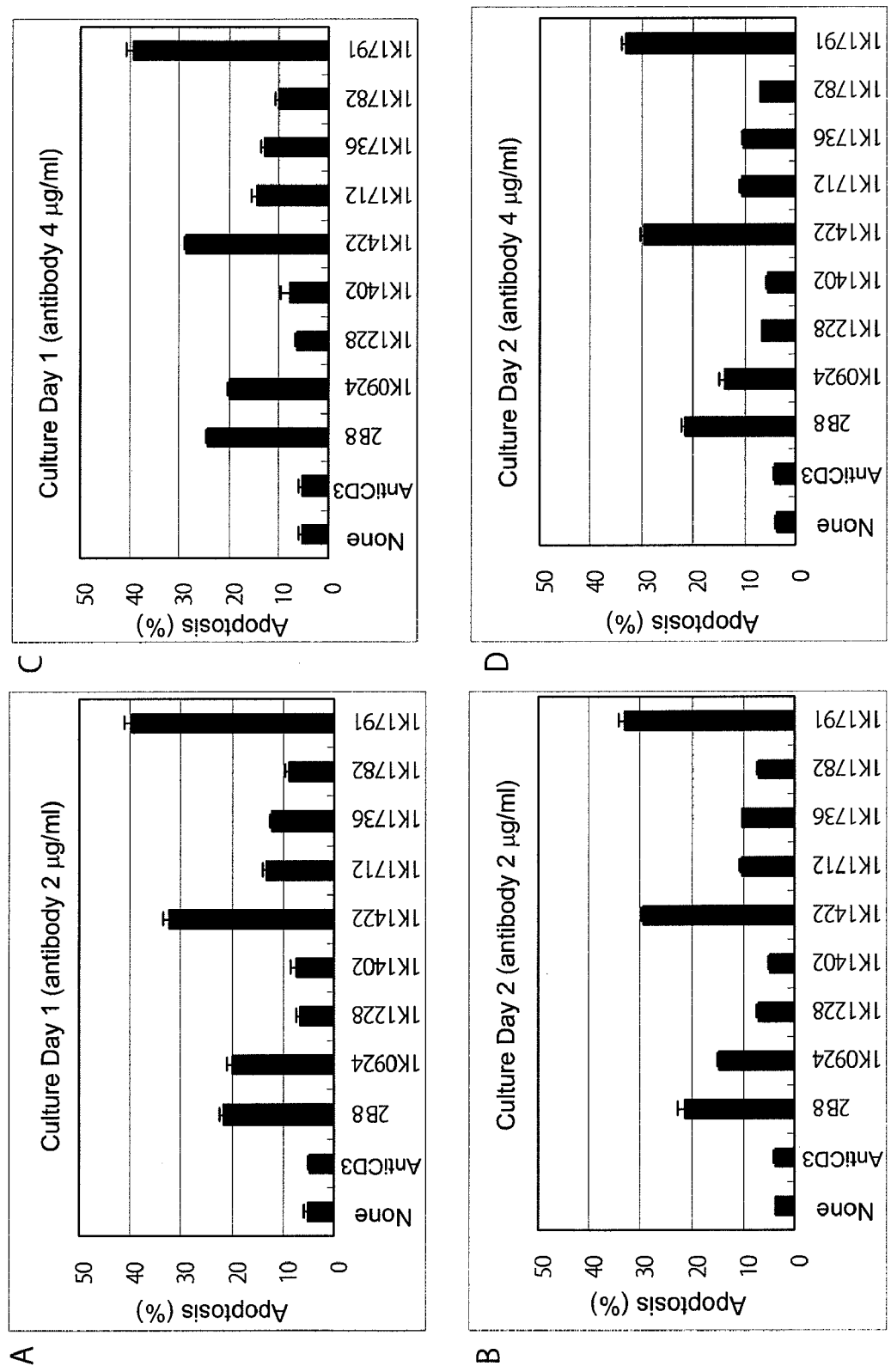
FIGS. 5A-D show results of apoptosis test using murine anti-CD20 monoclonal antibodies.

The measurement results of 8 kinds of the typical murine anti-CD20 monoclonal antibodies, positive control (2B8), and negative control (anti-CD3 antibody) are shown in FIG. 5. In general, the apoptosis inducing ability of 2B8 is said to be high. Even compared with this, the clone of which amino acid sequences of the H chain variable region and the L chain variable region were those of SEQ ID NOS: 2 and 8 (1K1791) showed a markedly higher apoptosis inducing activity. Cell death clearly due to apoptosis was also observed with the clones of which amino acid sequence of the H chain variable region and the L chain variable region were those of SEQ ID NOS: 1 and 7 (1K1422) and SEQ ID NOS: 15 and 17 (1K0924).

Biological Characteristic Test (2): Cell Growth Inhibition Test

Figure 6:
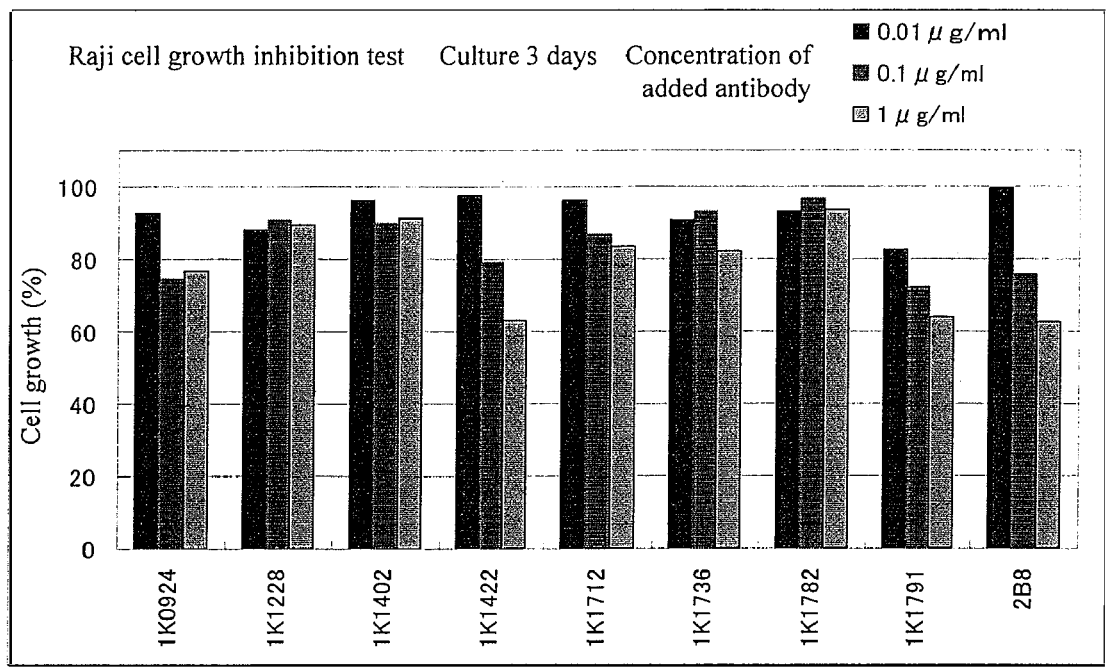
FIG. 6 Results of cell growth inhibition test using murine anti-CD20 monoclonal antibodies.

A $5\times10^4$ cells/ml Raji cell suspension was prepared with 10% FCS-added RPMI 1640 medium, and added to a 96-well plate in a volume of 100 μl/well, and culture was performed. After 24 hours, 50 μl/well of each antibody solution was added at an antibody concentration of 0.01 μg/ml, 0.1 μg/ml or 1 μg/ml, and culture was continued. Seventy two hours after the addition of the antibody, 10 μl/well of a color development solution, Cell Counting Kit-8 (Dojindo Laboratories, Cat. No. 343-07623, Lot SG076) was added, the cells were cultured for further 4 hours, and then absorbance was measured at 492 nm. The living cell counts of the typical 8 kinds of murine anti-CD20 monoclonal antibodies and the positive control (2B8) are shown in FIG. 6 as percentages based on that of the negative control (100%). The cell growth inhibitory effect can be estimated on the basis of the rate of the decreased living cell count compared with that of the negative control. Clear cell growth inhibition was observed with 1K0924, 1K1422, 1K1791 and 2B8 as the positive control, and the inhibition was particularly marked with 1K1791. This tendency was consistent with the results of the apoptosis induction test.

Preparation of Chimeric Antibodies

The genes encoding the H chain and L chain variable regions of each murine antibody were incorporated into pNOW-Ab, a high expression vector for CHO cell already containing the genes encoding human immunoglobulin H chain and L chain (κ) constant regions as a cassette. Each expression vector was transfected into CHO cells, and clones showing high productivity were selected for each antibody.

Test for Binding Property to CD20 Antigen of Chimeric antibodies

The prepared 8 kinds of chimeric anti-CD20 monoclonal antibodies were examined for reactivity to the human CD20 antigen by the CD20/CHO cell-ELISA. Rituximab (c2B8) was used as a positive control. The test results are shown in Table 2. The values measured in the cell-ELISA (A492) reflect intensity of the binding property. These antibodies showed affinity substantially comparable to or higher than that of the control except that c1K0924 and c1K1422 tended to show slightly lower affinity than that of the control.

TABLE 2

CD20/CHO cell-ELISA test of anti-CD20 chimeric antibodies

| Antibody | CD20/CHO cell-ELISA (A492) Antibody concentration (ng/ml) | | | | | |
|---|---|---|---|---|---|---|
| | 100 | 32 | 10 | 3 | 1 | 0 |
| c1K0924 | 1.423 | 0.724 | 0.391 | 0.186 | 0.094 | 0.032 |
| c1K1228 | 2.226 | 1.580 | 0.701 | 0.289 | 0.120 | 0.032 |
| c1K1402 | 2.449 | 1.621 | 0.737 | 0.349 | 0.116 | 0.032 |
| c1K1422 | 1.919 | 0.912 | 0.357 | 0.151 | 0.077 | |
| c1K1712 | 2.292 | 1.683 | 0.793 | 0.359 | 0.145 | |
| c1K1736 | 2.428 | 1.548 | 0.748 | 0.320 | 0.122 | |
| c1K1782 | 2.101 | 1.017 | 0.505 | 0.169 | 0.074 | |
| c1K1791 | 2.231 | 1.458 | 0.745 | 0.276 | 0.108 | |
| c2B8 | 2.147 | 1.143 | 0.536 | 0.226 | 0.088 | |

CDC Test of Chimeric Antibodies

The prepared 8 kinds of chimeric anti-CD20 monoclonal antibodies were examined for the CDC activity. Rituximab (c2B8) was used as a positive control. RC-K8 (obtained from Kochi Medical School) was used as the target cells. As a medium for use, RHB (basal medium: RPMI-1640, additives: 0.1% BSA, 20 mM HEPES (pH 7.2), 2 mM glutamine, 100 units/ml of penicillin G, 100 μg/ml of streptomycin) was prepared and used. The target cells were washed with RHB and resuspended at $10^6$ cells/ml. In a volume of 50 μl of each of the solutions of the test chimeric antibodies and rituximab having different concentrations, 50 μl of 4-fold diluted solution of a commercially available human complement (Quidel, San Diego, Calif., Cat. A113), and 50 μl of a cell suspension containing $10^6$ cells/ml were added to each well of a flat bottom 96-well tissue culture plate (black). The antibody concentration in the mixture of 150 μl/well was set at 0.1, 1 and 10 μg/ml. To promote complement-mediated cell lysis, the mixture was incubated under the conditions of 37° C. and 5% $CO_2$ for 2 hours. To the mixture was added 50 μl of alamar blue (undiluted, prescription of AccuMed International, Biosource, Cat. DAL1100), and the reaction was further allowed overnight under the same conditions. The plate was left at room temperature for 10 minutes to cool, and fluorescence was measured at 590 nm for emission with excitation at 530 nm by using a fluorescence microplate reader. The results were represented in terms of fluorescence intensity (RFU). The rate of CDC activity was calculated in accordance with the following equation:

% CDC activity=100×{RFU(antibody not added)−RFU(antibody added)}/{RFU(antibody not added]−RFU(Triton X-100 added)}

Figure 7:
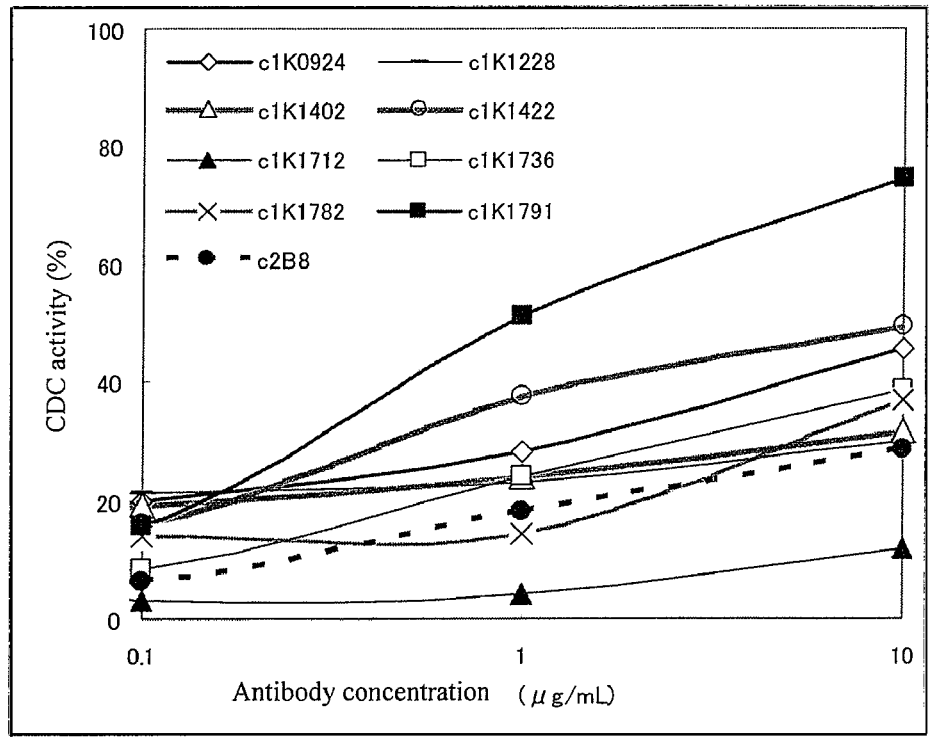
FIG. 7 Results of complement-dependent cytotoxicity test using chimeric anti-CD20 monoclonal antibodies.

The results are shown in FIG. 7. Except for c1K1712, the antibodies showed CDC activities substantially comparable to or higher than that of C2B2 as the positive control.

Preparation of Humanized Antibodies

Humanized antibodies were designed based on the variable region CDR of the murine anti-CD20 monoclonal antibody 1K1791. By performing structural analysis based on the amino acid sequences and further changing the designing method, 4 kinds of humanized sequences were prepared for each of the H chain and the L chain (Padlan EA, Mol. Immunol., Vol. 28, No 4/5, 489-498; Wu T T and Kabat E A, Mol. Immunol., Vol. 29, No 9, 1141-1146; Padlan E A et al., FASEB J., Vol. 9, 133-139). Antibodies were prepared with all possible combinations of the four types for each of the H chain and the L chain. These amino acid sequences are shown in SEQ ID NOS: 19 and 23, SEQ ID NOS: 19 and 24, SEQ ID NOS: 19 and 25, SEQ ID NOS: 19 and 26, SEQ ID NOS: 20 and 23, SEQ ID NOS: 20 and 24, SEQ ID NOS: 20 and 25, SEQ ID NOS: 20 and 26, SEQ ID NOS: 21 and 23, SEQ ID NOS: 21 and 24, SEQ ID NOS: 21 and 25, SEQ ID NOS: 21 and 26, SEQ ID NOS: 22 and 23, SEQ ID NOS: 22 and 24, SEQ ID NOS: 22 and 25, and SEQ ID NOS: 22 and 26 (FIGS. 8A and 8B).

The amino acid sequences of these 4 kinds of H chain variable regions and 4 kinds of L chain variable regions were converted into DNA (nucleotide) sequences with codons most frequently used in human gene sequences, and some of these nucleotides were changed considering suitability in the host CHO cells without changing the original amino acid residues (Kim C H et al., Gene, 1997, 15; 199 (1-2): 293-301). Specifically, used as the nucleotide sequences corresponding to the amino acid sequences were those of SEQ ID NO: 27 corresponding to SEQ ID NO: 19, SEQ ID NO: 28 corresponding to SEQ ID NO: 20, SEQ ID NO: 29 corresponding to SEQ ID NO: 21, SEQ ID NO: 30 corresponding to SEQ ID NO: 22, SEQ ID NO: 31 corresponding to SEQ ID NO: 23, SEQ ID NO: 32 corresponding to SEQ ID NO: 24, SEQ ID NO: 33 corresponding to SEQ ID NO: 25, and SEQ ID NO: 34 corresponding to SEQ ID NO: 26 (FIG. 8A and FIG. 8B). In these nucleotide sequences, nucleotides may be replaced with other nucleotides so long as the corresponding amino acid sequences are not altered.

Total 8 kinds of the nucleotide sequences of H chain variable regions (SEQ ID NOS: 27 to 30) and L chain variable regions (SEQ ID NOS: 31 to 34) were synthesized (Takara Shuzo Co., Ltd.) and incorporated into pNOW-Ab, an expression vector for mammalian cells containing a multicloning site. The expression vectors incorporated with each of these humanized antibody genes were transfected into CHO cells, and clones showing high productivity were selected for each antibody.

Figure 9:
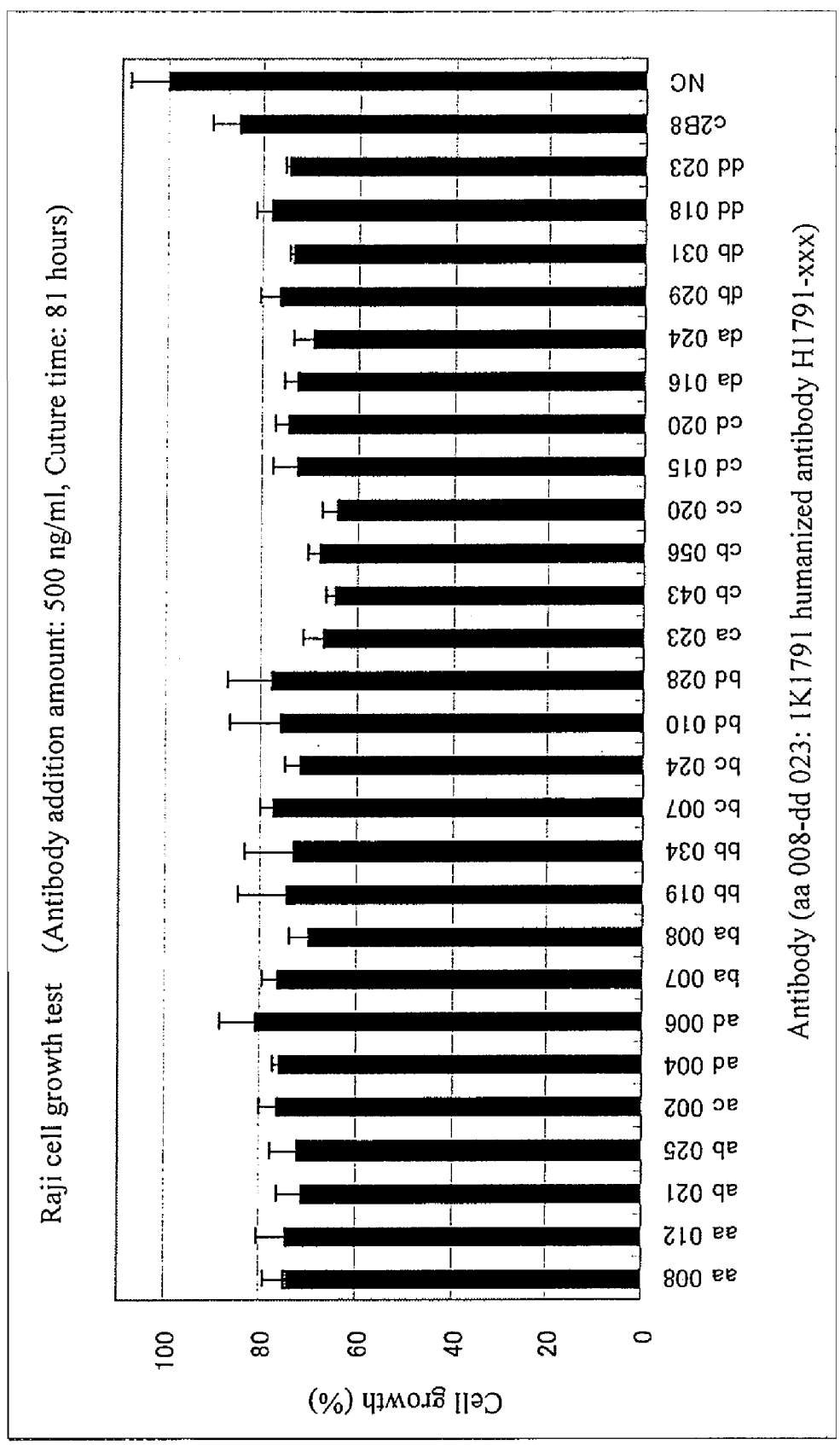
FIG. 9 Results of cell growth inhibition test using humanized anti-CD20 monoclonal antibodies.

Biological Characteristic and Cell Growth Inhibition Tests for Humanized Antibodies A suspension containing $5 \times 10^4$/ml of the Raji cells was prepared with 10% FCS-added RPMI 1640 medium, and added to a 96-well plate in a volume of 100 μl/well, and culture was performed. After 24 hours, 50 μl/well of each antibody solution was added at an antibody concentration of 0.5 μg/ml, and culture was continued. Seventy two hours after the addition of the antibody, 10 μl/well of a color development solution, Cell Counting Kit-8 (Dojindo Laboratories, Cat. No. 343-07623, Lot SG076) was added, culture was performed for further 4 hours, and then absorbance was measured at 492 nm. The living cell counts of 15 kinds (27 clones) out of 16 kinds of humanized antibodies derived from 1K1791 and c2B8 (other name of rituximab) as the positive control are shown in FIG. 9 as rates based on that of the negative control (100%). The cell growth inhibitory effect can be estimated on the basis of rate of decreased living cell count compared with that of the negative control, and the growth inhibitory effect was observed for all the clones in this test.

The names of monoclonal antibodies and the sequence numbers described in this specification and the appended drawings are summarized as follows.

TABLE 3

| Murine antibody name | H chain variable region | L chain variable region | Chimeric antibody name | Humanized variable region (H chain/L chain) |
|---|---|---|---|---|
| 1K1422 | SEQ ID NO: 1 | SEQ ID NO: 7 | c1K1422 | |
| 1K1791 | SEQ ID NO: 2 | SEQ ID NO: 8 | c1K1791 | SEQ ID NOS: 19 and 23 |
| | | | | SEQ ID NOS: 19 and 24 |
| | | | | SEQ ID NOS: 19 and 25 |
| | | | | SEQ ID NOS: 19 and 26 |
| | | | | SEQ ID NOS: 20 and 23 |
| | | | | SEQ ID NOS: 20 and 24 |
| | | | | SEQ ID NOS: 20 and 25 |
| | | | | SEQ ID NOS: 20 and 26 |
| | | | | SEQ ID NOS: 21 and 23 |
| | | | | SEQ ID NOS: 21 and 24 |
| | | | | SEQ ID NOS: 21 and 25 |
| | | | | SEQ ID NOS: 21 and 26 |
| | | | | SEQ ID NOS: 22 and 23 |
| | | | | SEQ ID NOS: 22 and 24 |
| | | | | SEQ ID NOS: 22 and 25 |
| | | | | SEQ ID NOS: 22 and 26 |
| 1K1712 | SEQ ID NO: 3 | SEQ ID NO: 9 | c1K1712 | |
| 1K1402 | SEQ ID NO: 4 | SEQ ID NO: 10 | c1K1402 | |
| 1K1736 | SEQ ID NO: 5 | SEQ ID NO: 11 | c1K1736 | |
| 1K1782 | SEQ ID NO: 6 | SEQ ID NO: 12 | c1K1782 | |
| 1K0924 | SEQ ID NO: 15 | SEQ ID NO: 17 | c1K0924 | |
| 1K1228 | SEQ ID NO: 16 | SEQ ID NO: 18 | c1K1228 | |

The hybridomas producing these monoclonal antibodies were named on the basis of the names of the antibodies produced thereby, and internationally deposited at the National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Mar. 28, 2006 under the provisions of the Budapest Treaty, and assigned accession numbers of FERM BP-10587 (1K1422), FERM BP-10591 (1K1791), FERM BP-10588 (1K1712), FERM BP-10586 (1K1402), FERM BP-10589 (1K1736), FERM BP-10590 (1K1782), FERM BP-10584 (1K0924), and FERM BP-10585 (1K1228).

INDUSTRIAL APPLICABILITY

The present invention provides a monoclonal antibody having biological activities suitable for use as a therapeutic agent.

What is claimed is:

1. A murine anti-CD20 monoclonal antibody having cell growth inhibitory activities including apoptosis against human CD20 antigen expressing cells in culture of the CD20 antigen expressing cells without effector cells, wherein the amino acid sequences of variable regions of the H chain and the L chain are SEQ ID NOS: 1 and 7 or SEQ ID NOS: 2 and 8.

2. A hybridoma producing the anti-CD20 monoclonal antibody according to claim 1.

3. A chimeric anti-CD20 monoclonal antibody, wherein the amino acid sequences of the variable regions of the anti-CD20 monoclonal antibody according to claim 1 and the amino acid sequences of the constant regions of human immunoglobulin are fused, respectively.

4. A humanized anti-CD20 monoclonal antibody comprising all of the variable region CDRs of the H chain of the antibody of claim 1 and all of the variable region CDRs of the L chain of the antibody of claim 1 and an amino acid sequence of human immunoglobulin.

5. The humanized anti-CD20 monoclonal antibody according to claim 4, wherein the combination of the amino acid sequences of the H chain variable region and the L chain variable region is a combination of SEQ ID NOS: 19 and 23, SEQ ID NOS: 19 and 24, SEQ ID NOS: 19 and 25, SEQ ID NOS: 19 and 26, SEQ ID NOS: 20 and 23, SEQ ID NOS: 20 and 24, SEQ ID NOS: 20 and 25, SEQ ID NOS: 20 and 26, SEQ ID NOS: 21 and 23, SEQ ID NOS: 21 and 24, SEQ ID NOS: 21 and 25, SEQ ID NOS: 21 and 26, SEQ ID NOS: 22 and 23, SEQ ID NOS: 22 and 24, SEQ ID NOS: 22 and 25, or SEQ ID NOS: 22 and 26.

6. The anti-CD20 monoclonal antibody according to claim 3 or 4, which has cytotoxicity against CD20 antigen expressing cells in the presence of a human complement or effector cells.

7. A mammalian cell comprising a nucleotide sequence encoding the amino acid sequence of the anti-CD20 monoclonal antibody according to claim 3 or 4.

8. The mammalian cell according to claim 7, which a CHO cell.

9. A diagnostic agent comprising the anti-CD20 monoclonal antibody according to claim 1 as an active ingredient.

10. A therapeutic agent comprising the anti-CD20 monoclonal antibody according to any one of claim 3 or 4 as an active ingredient.

* * * * *

UNITED STATES PATENT AND TRADEMARK OFFICE
CERTIFICATE OF CORRECTION

| | | |
|---|---|---|
| PATENT NO. | : 8,101,179 B2 | |
| APPLICATION NO. | : 11/910429 | |
| DATED | : January 24, 2012 | |
| INVENTOR(S) | : Numazaki et al. | |

It is certified that error appears in the above-identified patent and that said Letters Patent is hereby corrected as shown below:

Drawings, Sheet 8 of 8, Fig. 9, Line 1, "Cuture time:" should be changed to --Culture time:--

Column 2, Line 46, "63:" should be changed to --63: 1424-1433.--

Column 2, Line 47, "1644" should be changed to --1644-52--

Column 2, Line 54, "99:" should be changed to --99: 1314-1319--

Column 2, Line 56, "107:" should be changed to --107: 176-182--

Column 2, Line 65, "92:" should be changed to --92: 1927-1932--

Column 3, Line 1, "Heamatologica, 2002," should be changed to --Haematologica, 2002,--

Column 8, Line 50, "(Qi, V T" should be changed to --(Oi, V T--

Column 10, Line 39, "of 0.2 um and" should be changed to --of 0.2 µm and--

Column 12, Line 42, "added]-RFU(Triton X-100 added)}" should be changed to
--added)-RFU(Triton X-100 added)}--

Column 40, Line 39, "which a CHO" should be changed to --which is a CHO--

Signed and Sealed this
Twenty-fourth Day of July, 2012

David J. Kappos
*Director of the United States Patent and Trademark Office*